(12) United States Patent
Miyashita et al.

(10) Patent No.: US 9,601,701 B2
(45) Date of Patent: Mar. 21, 2017

(54) ORGANIC COMPOUND AND ORGANIC LIGHT-EMITTING DEVICE

(71) Applicant: CANON KABUSHIKI KAISHA, Tokyo (JP)

(72) Inventors: Hirokazu Miyashita, Tokyo (JP); Jun Kamatani, Tokyo (JP); Tetsuya Kosuge, Yokohama (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 339 days.

(21) Appl. No.: 14/352,040

(22) PCT Filed: Oct. 2, 2012

(86) PCT No.: PCT/JP2012/076062
§ 371 (c)(1),
(2) Date: Apr. 15, 2014

(87) PCT Pub. No.: WO2013/058137
PCT Pub. Date: Apr. 25, 2013

(65) Prior Publication Data
US 2014/0264312 A1    Sep. 18, 2014

(30) Foreign Application Priority Data

Oct. 17, 2011   (JP) ................. 2011-227974

(51) Int. Cl.
*H01L 51/50* (2006.01)
*H01L 29/08* (2006.01)
(Continued)

(52) U.S. Cl.
CPC .......... *H01L 51/0058* (2013.01); *C07C 15/20* (2013.01); *C09K 11/06* (2013.01); *G03G 15/04036* (2013.01); *H01L 27/3244* (2013.01); *H01L 51/006* (2013.01); *H01L 51/0056* (2013.01); *H01L 51/0072* (2013.01);
(Continued)

(58) Field of Classification Search
CPC ..... C07C 15/20; C07C 2103/54; C09K 11/06; C09K 2211/1011; G03G 15/04036; H01L 27/3244; H01L 51/0052; H01L 51/0054; H01L 51/0056; H01L 51/0058;
(Continued)

(56) References Cited

U.S. PATENT DOCUMENTS

| 2004/0076853 | A1* | 4/2004 | Jarikov | C09K 11/06 428/690 |
| 2008/0213624 | A1* | 9/2008 | Lecloux | C09K 11/06 428/691 |
| 2012/0286251 | A1 | 11/2012 | Park et al. | |

FOREIGN PATENT DOCUMENTS

| JP | 2008001674 A | 1/2008 |
| JP | 2010034454 A | 2/2010 |

OTHER PUBLICATIONS

Alonso et al., Angew. Chem. Int. Ed., (2012), vol. 51, pp. 173-177.*
(Continued)

*Primary Examiner* — Dawn Garrett
(74) *Attorney, Agent, or Firm* — CANON USA, INC. IP Division

(57) ABSTRACT

The present invention relates to a novel stable benzo[h] hexaphene compound and an organic light-emitting device including the compound. The present invention provides a benzo[h]hexaphene shown in claim 1.

12 Claims, 1 Drawing Sheet

(51) Int. Cl.
  *C07C 13/48* (2006.01)
  *C07C 211/00* (2006.01)
  *C07C 22/00* (2006.01)
  *C07D 213/04* (2006.01)
  *C07C 255/00* (2006.01)
  *H01L 51/00* (2006.01)
  *C07C 15/20* (2006.01)
  *C09K 11/06* (2006.01)
  *H05B 33/14* (2006.01)
  *G03G 15/04* (2006.01)
  *H01L 27/32* (2006.01)
  *H05B 33/08* (2006.01)

(52) U.S. Cl.
  CPC ..... *H01L 51/5012* (2013.01); *H05B 33/0896* (2013.01); *H05B 33/14* (2013.01); *C07C 2103/54* (2013.01); *C09K 2211/1011* (2013.01); *H01L 51/0052* (2013.01); *H01L 51/0054* (2013.01); *H01L 51/0059* (2013.01)

(58) Field of Classification Search
  CPC ............... H01L 51/0059; H01L 51/006; H01L 51/0072; H01L 51/5012; H05B 33/0896
  See application file for complete search history.

(56) References Cited

OTHER PUBLICATIONS

Rachin, E., "Theoretic Cancerogenicity of Seven-Ring Benzene Hydrocarbons", Bulgarian Academy of Sciences, Communications of the Department of Chemistry, (1988), pp. 69-77, vol. 21, No. 1.

Goodwin, et al., "A Simple Molecular-Orbital Study of the β=, α=, and p= Bands in Triphenylenes", Theoretica Chimica Acta (Berl.), (1964) vol. 2 No. 1, pp. 75-83.

* cited by examiner

ORGANIC COMPOUND AND ORGANIC LIGHT-EMITTING DEVICE

TECHNICAL FIELD

The present invention relates to a novel organic compound and an organic light-emitting device including the organic compound.

BACKGROUND ART

An organic light-emitting device includes an anode, a cathode, and an organic compound layer disposed therebetween. Electrons and holes are injected from the electrodes into the organic compound layer to generate excitons of the light-emitting organic compound in the organic compound layer, and the organic light-emitting device emits light when the excitons return to the ground state.

The organic light-emitting device is also referred to as organic electroluminescent device or organic EL device. Organic light-emitting devices have remarkably progressed recently, and low driving voltages, high luminance, various emission wavelengths, rapid response, and reductions in size and weight of light-emitting devices are possible. However, in the organic light-emitting devices, the organic compound itself emits light, and thereby the lifetime is short, and there is a demand for further extension of the lifetime.

As a fluorescence-emitting material used in an organic light-emitting device, PTL 1 proposes a compound having a basic skeleton of dibenzo[a,c]tetracene shown as H1 below. NPL 1 reports on molecular orbital calculation of benzo[h]hexaphene shown as H2 below.

[Chem. 1]

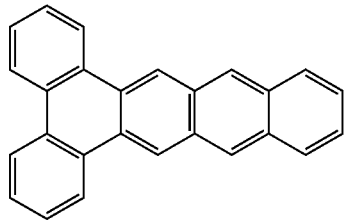

H1

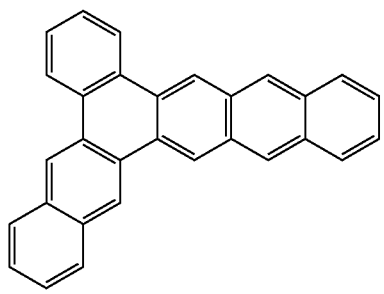 [SMILES: c1ccc2cc3cc4c(cc3cc2c1)c1ccccc1c1cc2ccccc2cc14]

H2

The compound disclosed in PTL 1 has a highly symmetrical basic skeleton and is thereby highly crystallizable. Consequently, a thin film formed of this compound tends to cause a change in film structure as a result of crystallization.

The compound disclosed in NPL 2 is an unsubstituted fused ring compound and is thereby highly crystallizable. In addition, the compound itself is readily oxidized and is thus unstable.

Furthermore, NPL 2 merely shows the organic compound represented by H2 as a model for molecular orbital calculation and is not referred to as a material for organic light-emitting devices.

CITATION LIST

Patent Literature

PTL 1 Japanese Patent Laid-Open No. 2008-001674

Non Patent Literature

NPL 1 Theoretica Chimica Acta, 2(1), 75-83, 1964

SUMMARY OF INVENTION

Accordingly, the present invention provides a benzo[h]hexaphene represented by the following Formula (1):

[Chem. 2]

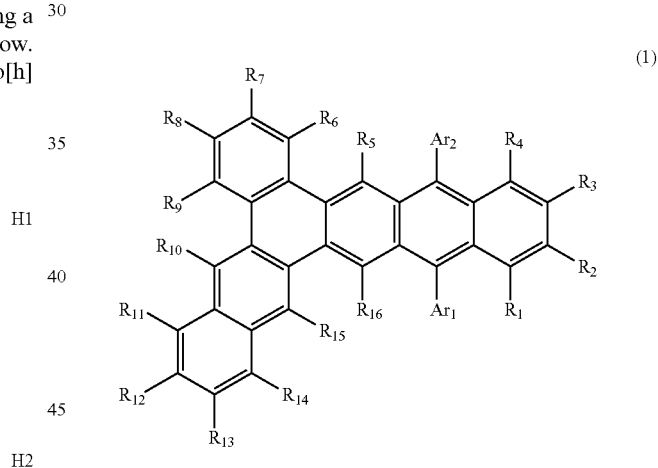

(1)

In Formula (1), $R_1$ to $R_{16}$ each independently selected from hydrogen and halogen atoms and methyl, ethyl, iso-propyl, t-butyl, cyano, diphenylamino, pyridyl, phenyl, biphenyl, terphenyl, and naphthyl groups.

The diphenylamino, pyridyl, phenyl, biphenyl, terphenyl, and naphthyl groups optionally have substituents of methyl, ethyl, iso-propyl, t-butyl, or fluorine groups.

$Ar_1$ and $Ar_2$ are any of phenyl, biphenyl, terphenyl, and naphthyl groups.

$Ar_1$ and $Ar_2$ optionally have substituents of methyl, ethyl, iso-propyl, t-butyl, or fluorine groups.

Accordingly, the organic compound of the present invention has low molecular symmetry. Thus, the present invention can provide an organic compound exhibiting low crystallizability and being stable against oxidation and also can provide an organic light-emitting device including the organic compound to show a long emission lifetime.

DESCRIPTION OF EMBODIMENT

Figure 1:
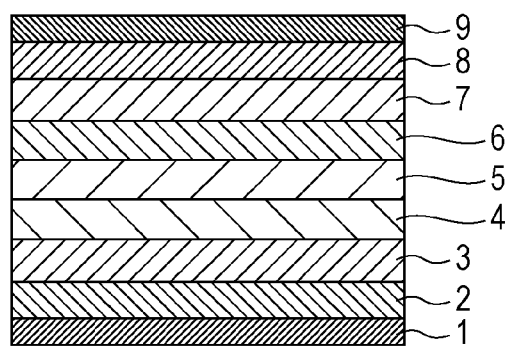
FIG. 1 is a schematic diagram illustrating an example of the organic light-emitting device of a light-emitting layer lamination type according to an embodiment.

The organic compound of the present invention is a benzo[h]hexaphene represented by the following Formula (1):

[Chem. 3]

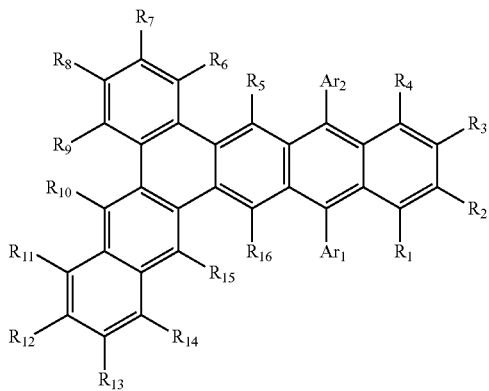

(1)

In Formula (1), $R_1$ to $R_{16}$ each independently selected from hydrogen and halogen atoms and methyl, ethyl, iso-propyl, t-butyl, cyano, diphenylamino, pyridyl, phenyl, biphenyl, terphenyl, and naphthyl groups.

The diphenylamino, pyridyl, phenyl, biphenyl, terphenyl, and naphthyl groups optionally have substituents of methyl, ethyl, iso-propyl, t-butyl, or fluorine groups.

$Ar_1$ and $Ar_2$ are any of phenyl, biphenyl, terphenyl, and naphthyl groups.

$Ar_1$ and $Ar_2$ optionally have substituents of methyl, ethyl, iso-propyl, t-butyl, or fluorine groups.

Though the organic compound according to the present invention has a basic skeleton having high flatness, the presence of $Ar_1$ and $Ar_2$ substituents inhibits molecular packing.

In addition, $Ar_1$ and $Ar_2$ are introduced to highly reactive sites of the basic skeleton of the organic compound according to the present invention to inhibit the reactivity of the sites. Consequently, the organic compound according to the present invention is stable against oxidation.

In the embodiment, the term "basic skeleton" refers to a fused ring structure having conjugation. That is, the basic skeleton of the organic compound according to the present invention is the same as that of the compound represented by Formula (3) shown below.

Comparison of the Compound of the Present Invention with Other Organic Compounds The organic compound according to the present invention will be compared with compounds represented by Formulae (2) and (3).

The compound represented by Formula (2) is a compound having a basic skeleton described in PTL 1 and substituents such as those of Example Compound A1 according to the embodiment.

The compound represented by Formula (3) is a compound described in NPL 1.

[Chem. 4]

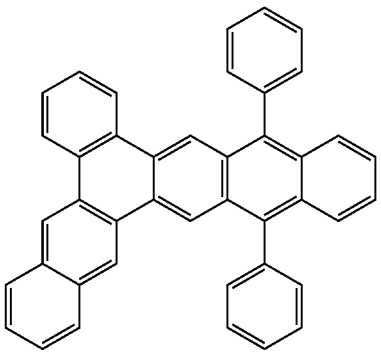 [SMILES: c1ccc(-c2c3ccccc3c(-c3ccccc3)c3cc4c5cc6ccccc6cc5c5ccccc5c4cc23)cc1]

A1

[Chem. 5]

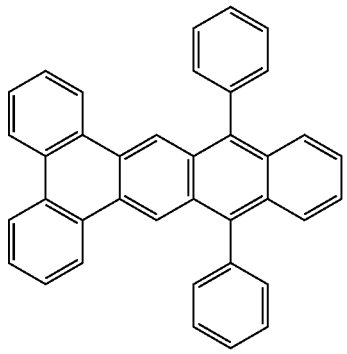

(2)

[Chem. 6]

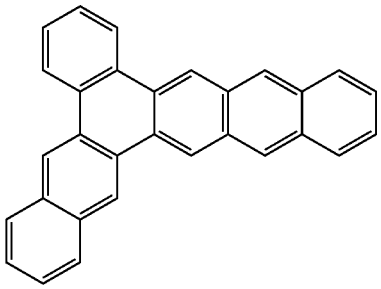 [SMILES: c1ccc2cc3cc4c(cc3cc2c1)c1ccccc1c1cc2ccccc2cc14]

(3)

The organic compound to be used for the organic light-emitting device is required to be capable of forming a thin film having a high amorphous property to show excellent film properties and high thermal stability. The term "high amorphous property" is also referred to be hardly crystallizable.

The organic compound according to the present invention has a less symmetric basic skeleton compared with Compound (2) and is inhibited from molecular packing. As a result, a thin film having a high amorphous property can be formed.

In the embodiment, the Example Compound A1 according to the embodiment and Compound (2) are compared for symmetry of the molecular structures by group theory.

[Chem. 7]

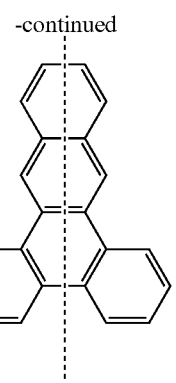

Benzo[f]tetraphene skeleton

D3$_h$

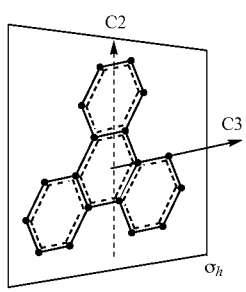

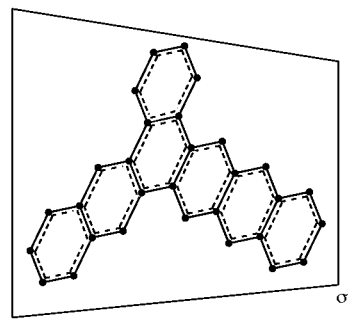

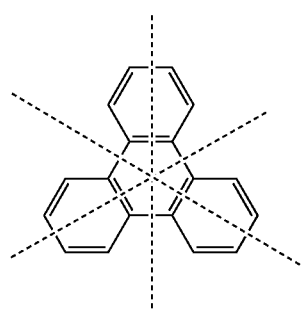

Triphenylene skeleton

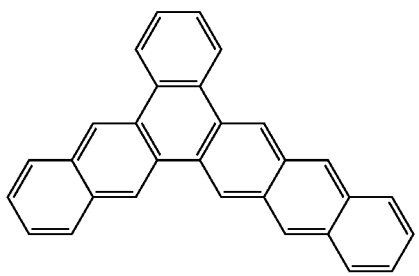

Benzo[h]hexaphene skeleton

C2$_v$

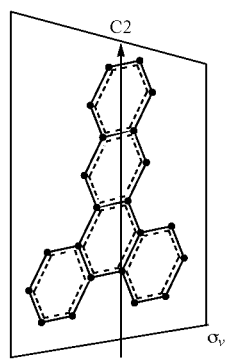

For example, the triphenylene skeleton has a three-fold rotation axis (C3) in the direction perpendicular to the molecular plane and has a two-fold rotation axis (C2) and symmetry plane ($\sigma_h$) orthogonal to the three-fold rotation axis. Accordingly, the triphenylene skeleton belongs to a D$_{3h}$ point group.

The benzo[f]tetraphene skeleton has a two-fold rotation axis (C2) in the longitudinal axis direction of the molecular plane and a symmetry plane ($\sigma_v$) containing the two-fold rotation axis. Accordingly, the benzo[f]tetraphene skeleton belongs to a C$_{2v}$ point group.

In contrast, the benzo[h]hexaphene skeleton does not have a rotation axis and has a symmetry plane ($\sigma$) containing a molecular plane. Accordingly, the benzo[h]hexaphene skeleton belongs to a Cs point group.

Consequently, the molecular symmetry decreases in the order of the triphenylene skeleton, the benzo[f]tetraphene skeleton, and the benzo[h]hexaphene skeleton.

In a film made of a compound having lower symmetry, the molecular arrangement is readily disordered compared with a case of a compound having higher symmetry, and therefore the molecules are prevented from regularly overlapping each other, i.e., from molecular packing.

A thin film formed of a compound that is prevented from molecular packing is hardly crystallized to exhibit a high amorphous property. That is, a thin film formed of less symmetric molecules has a higher amorphous property.

Table 1 shows grouping based on the group theory of the compounds. The symmetry of Compound (2) belongs to $C_{2v}$, whereas the symmetry of Example Compound A1 belongs to $C_s$.

Thus, Example Compound A1 is a less symmetric molecule and therefore can form a thin film having a high amorphous property to show more excellent film properties.

Example Compound A1, which is an organic compound according to the present invention, has a higher glass transition temperature (Tg) than that of Compound (2). That is, the organic compound according to the present invention is thermally stable.

The Tg is a temperature at which a molecule starts the micro-Brownian motion without changing the center of gravity. In a molecule having a low Tg, the micro-Brownian motion is easily induced.

Accordingly, in a thin film formed of molecules having a low Tg, rearrangement of the molecules tends to occur in the thin film. This rearrangement enhances crystallization to decrease the amorphous property of the thin film. That is, an amorphous thin film having a high Tg has high thermal stability.

The organic compound having a high Tg can be used for an organic light-emitting device.

An organic compound having a high Tg can be designed by increasing the molecular weight of the organic compound or enhancing the intermolecular interaction.

In an organic compound for an organic light-emitting device, since higher sublimability is advantageous for producing an organic light-emitting device, the intermolecular interaction is required to be appropriately enhanced without highly increasing the molecular weight.

As shown in Table 1, Example Compound A1 has a larger molecular weight by 50 and a higher Tg by 19° C. than those of Compound (2).

Thus, Example Compound A1 has a high Tg and can therefore form an amorphous thin film having further excellent thermal stability. Accordingly, the organic compound according to the present invention can be used for organic light-emitting devices.

TABLE 1

| Compound | Structural formula | Point group | Molecular weight | Tg (° C.) |
|---|---|---|---|---|
| Compound (2) | | $C_{2v}$ | $C_{38}H_{24}$ = 480.60 | 117 |
| Example Compound A1 | | $C_s$ | $C_{42}H_{26}$ = 530.66 | 136 |

Though the basic skeleton of the organic compound according to the present invention has high flatness, as shown in Formula (1), the organic compound has $Ar_1$ and $Ar_2$ and is thereby prevented from molecular packing. Though this effect can be obtained even in the case of having only either $Ar_1$ or $Ar_2$ substituent, a higher effect can be obtained when the compound have both substituents.

The positions of Ar₁ and Ar₂ will now be described.

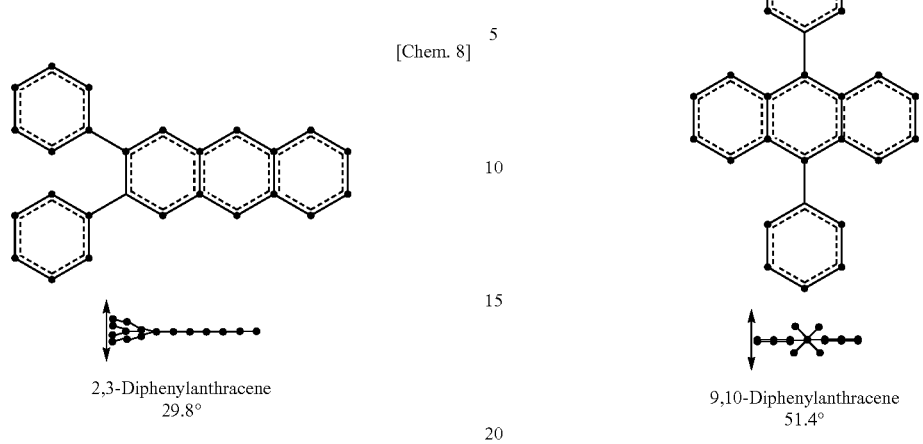

2,3-Diphenylanthracene
29.8°

9,10-Diphenylanthracene
51.4°

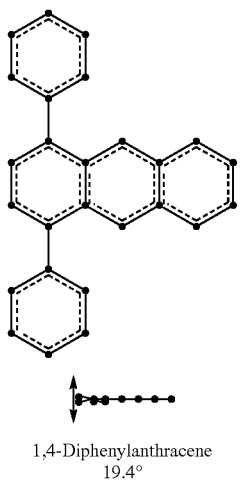

1,4-Diphenylanthracene
19.4°

For example, in diphenylanthracene, the dihedral angles of phenyl groups with respect to the molecular plane vary depending on the substitutional positions of the two phenyl groups.

The dihedral angle of the phenyl group is the maximum in a structure having two phenyl groups at the 9- and 10-positions. The substitutional position showing the maximum dihedral angle can most effectively prevent molecular packing.

As shown in Table 2, Example Compound A1 has bulky substituents at positions to effectively prevent molecular packing and thereby has a high amorphous property.

In contrast, Compound (3) is unsubstituted and therefore has a low amorphous property. Thus, compared with Compound (3), Example Compound A1 has lower crystallizability and can form a film having a higher amorphous property as the film properties.

Accordingly, the organic compound of the present invention can be used for organic light-emitting devices.

TABLE 2

| Compound | Structural formula | Molecular plane: perpendicular direction | Molecular plane: parallel direction |
|---|---|---|---|
| Compound (3) | | | |

TABLE 2-continued

| Compound | Structural formula | Molecular plane: perpendicular direction | Molecular plane: parallel direction |
|---|---|---|---|
| Example Compound A1 | | | |

Furthermore, the organic compound according to the present invention has substituents at specific positions to inhibit the reactivity of highly reactive sites in the basic skeleton and is therefore stable against oxidation.

Example Compound A1, which is an organic compound according to the present invention, is more stable against oxidation as a compound itself compared with Compound (3). Causes of this will be described from the points of structure and stability of the compounds.

Among fused ring compounds, compounds having a structure in which a plurality of benzene rings are linearly fused are called acene. A characteristic of the acene is that the structural stability decreases with an increase in the number of the fused benzene rings.

For example, in anthracene, which is a typical acene compound, the benzene rings at both ends function as electron donors to increase the electron density of the central benzene ring.

Thus, the central benzene ring of anthracene tends to be oxidized. That is, the active sites unstable against oxidation in anthracene are the 9- and 10-positions at the center.

[Chem. 9]

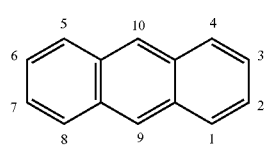

The active sites unstable against oxidation can be stabilized by introducing substituents thereto to reduce the reactivity through steric hindrance of the substituents.

That is, though a fused ring compound having a structure in which a plurality benzene rings are linearly fused, such as acene, is unstable due to the active sites, the stability against oxidation can be enhanced by introducing substituents to the active sites of the fused ring compound.

As shown in Table 3, Compound (3) partially has a structure having linearly fused unsubstituted benzene rings, has active sites at the substitutional positions indicated with the symbol *, and is unstable against oxidation.

In contrast, Example Compound A1 according to the present invention has bulky phenyl groups at the active sites as substituents and is therefore stable against oxidation.

TABLE 3

| Compound | Existence of active site in molecular structure |
|---|---|
| Compound (3) | |
| Example Compound A1 | |

As described above, Example Compound A1, which is an organic compound according to the present invention, has substituents at active sites and thereby shows higher stability against an oxidation-reduction reaction than Compound (3).

Accordingly, the organic compound according to the present invention, Example Compound A1, has a basic skeleton having low symmetry and high flatness and also has substituents introduced at effective sites and thereby can form an amorphous thin film suitable for organic light-emitting devices, compared with films formed of Compound (2) and Compound (3).

Furthermore, Example Compound A1 has substituents at the active sites and is thereby more stable as a compound itself compared with Compound (3).

That is, the organic compound according to the present invention has $Ar_1$ and $Ar_2$ as shown in Formula (1) and is therefore prevented from molecular packing to be stable against oxidation.

As a result, the organic compound according to the present invention can provide an organic light-emitting device having a longer lifetime compared with those of Compound (2) and Compound (3).

The organic compound according to the present invention can be used as a guest or host material of a light-emitting layer of an organic light-emitting device.

Throughout the specification, the host material is a compound having a largest weight ratio among the compounds constituting a light-emitting layer, and the guest material is a compound having a smaller weight ratio than that of the host material and bearing main light emission among the compounds constituting the light-emitting layer. The assist material is a compound having a smaller weight ratio than that of the host material and assisting the light emission of the guest material among the compounds constituting a light-emitting layer.

The guest material is also referred to as a dopant, and the assist material is also referred to as a second host material.

The organic compound according to the present invention may be contained in a layer other than the light-emitting layer, i.e., in a hole-injecting layer, hole-transporting layer, electron-transporting layer, electron-injecting layer, or any other layer.

The organic compound according to the present invention can be used as a host material, in particular, as a host material of a green- or red-light-emitting layer or a white-light-emitting device.

In the embodiment, the green region refers to a wavelength region of 490 nm or more and 530 nm or less of the maximum emission peak; and the red region refers to a wavelength region of 580 nm or more and 630 nm or less of the maximum emission peak.

The organic compound according to the present invention has a high HOMO and can therefore easily inject holes from an electrode. Accordingly, the organic compound can be used in a hole-injecting layer.

The high HOMO of the organic compound according to the present invention is due to the molecular structure composed of only six-membered rings.

Examples of Organic Compound According to the Present Invention

Specific examples of the organic compound according to the present invention are shown below, but the present invention is not limited to these compounds.

[Chem. 10]

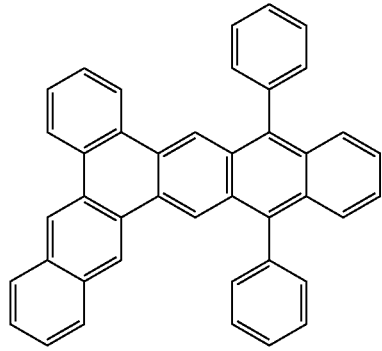 [SMILES: c1ccc(-c2c3ccccc3c(-c3ccccc3)c3cc4c5cc6ccccc6cc5c5ccccc5c4cc23)cc1]

A1

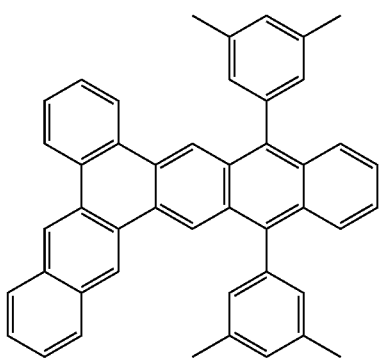

A2

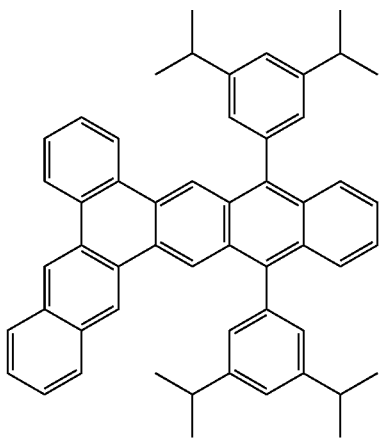

A3

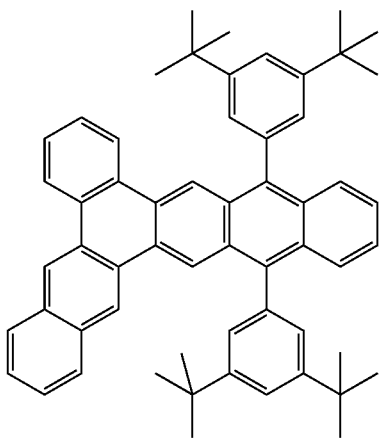 [SMILES: CC(C)(C)c1cc(-c2c3ccccc3c(-c3cc(C(C)(C)C)cc(C(C)(C)C)c3)c3cc4c5cc6ccccc6cc5c5ccccc5c4cc23)cc(C(C)(C)C)c1]

A4

A5
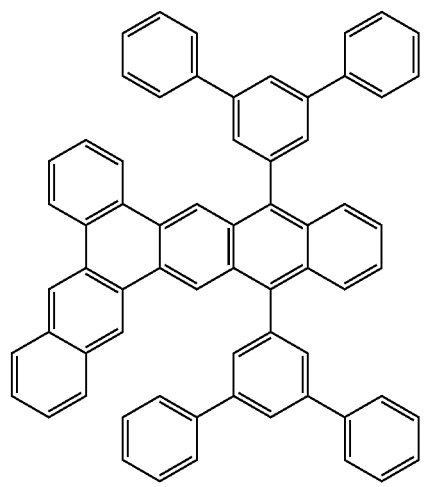
A6
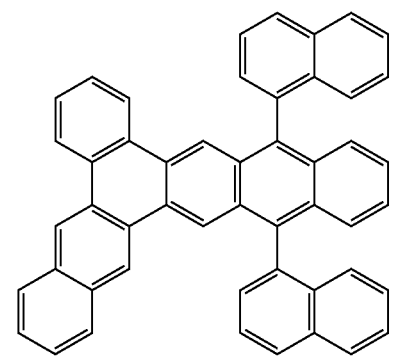 [SMILES: c1ccc2cc3c(cc2c1)c1ccccc1c1cc2c(-c4cccc5ccccc45)c4ccccc4c(-c4cccc5ccccc45)c2cc31]
A7
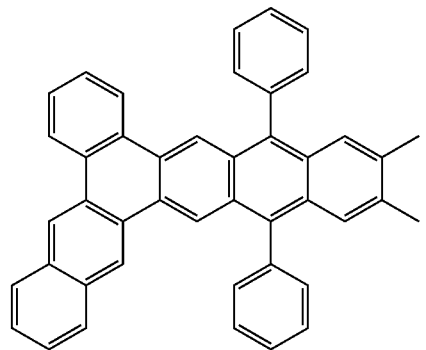 [SMILES: Cc1cc2c(-c3ccccc3)c3cc4c5ccccc5c5cc6ccccc6cc5c4cc3c(-c3ccccc3)c2cc1C]
A8
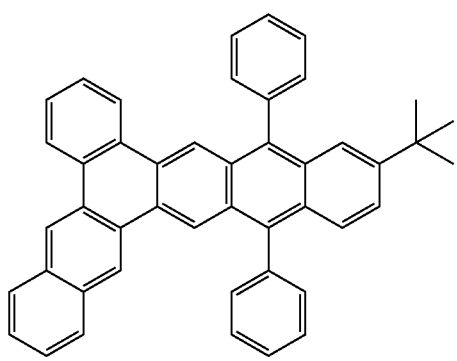
A9
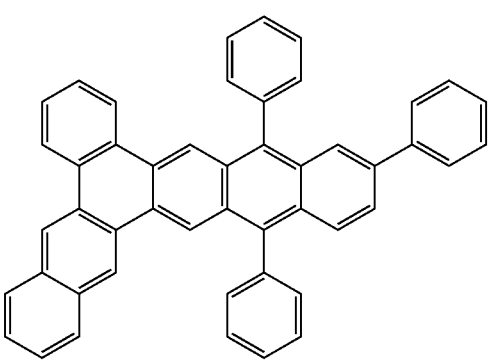 [SMILES: c1ccc(-c2ccc3c(-c4ccccc4)c4cc5c6cc7ccccc7cc6c6ccccc6c5cc4c(-c4ccccc4)c3c2)cc1]
A10
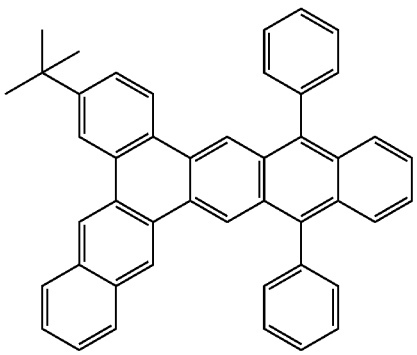 [SMILES: CC(C)(C)c1ccc2c(c1)c1cc3ccccc3cc1c1cc3c(-c4ccccc4)c4ccccc4c(-c4ccccc4)c3cc21]
A11
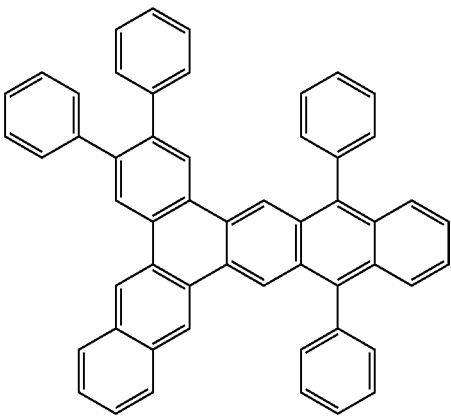 [SMILES: c1ccc(-c2cc3c(cc2-c2ccccc2)c2cc4c(-c5ccccc5)c5ccccc5c(-c5ccccc5)c4cc2c2cc4ccccc4cc32)cc1]
A12
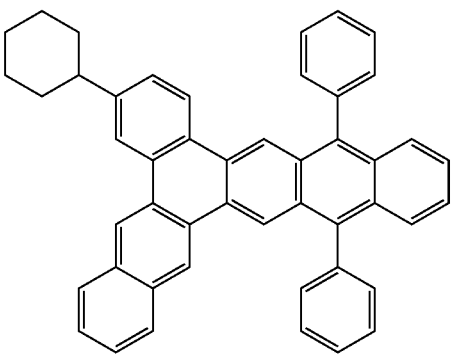

A13
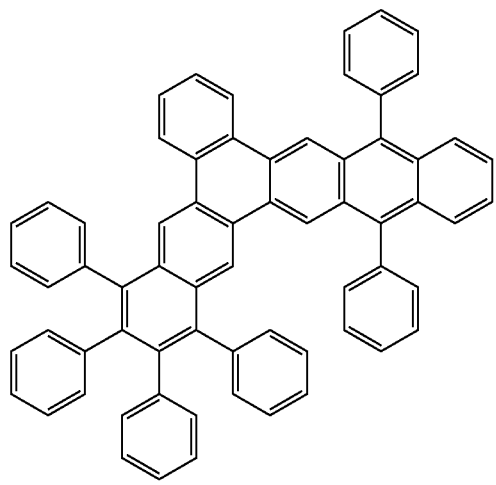
A14
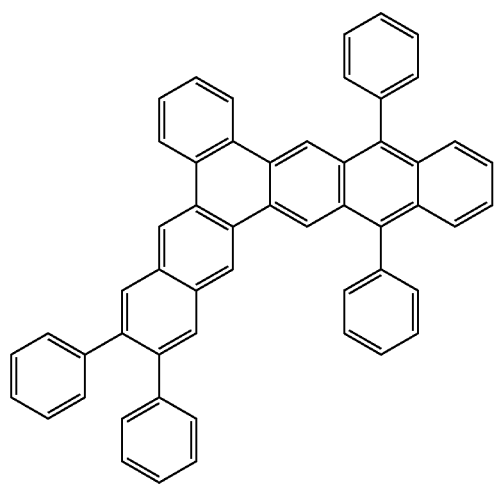
A15
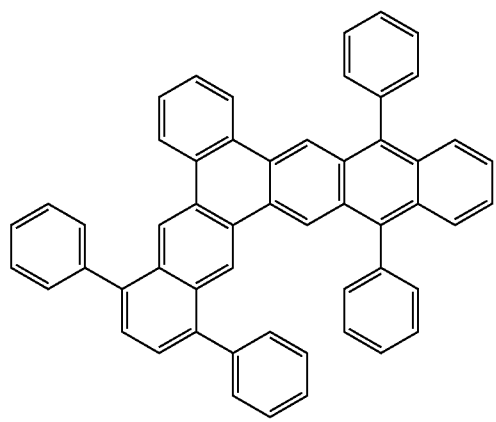 [SMILES: c1ccc(-c2ccc(-c3ccccc3)c3cc4c(cc23)c2ccccc2c2cc3c(-c5ccccc5)c5ccccc5c(-c5ccccc5)c3cc42)cc1]
[Chem. 11]
A16
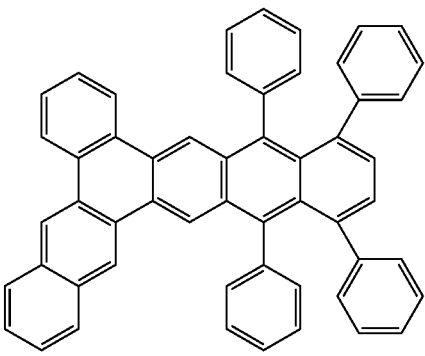
A17
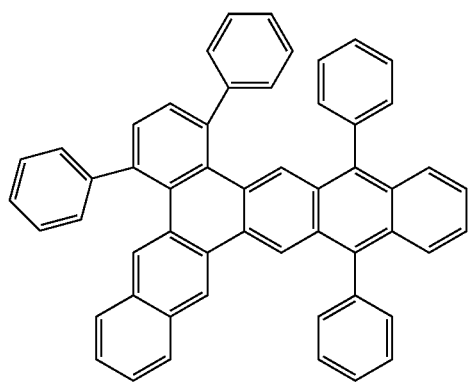
A18
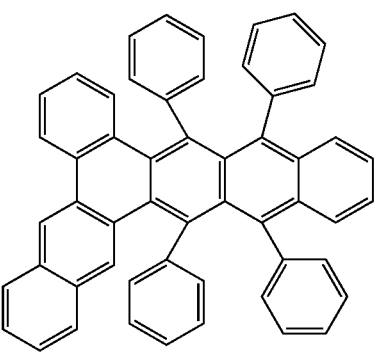
A19
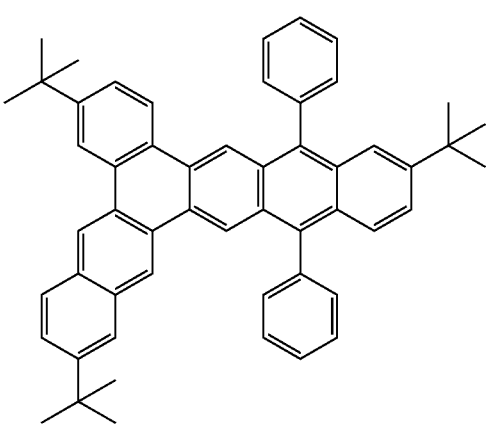

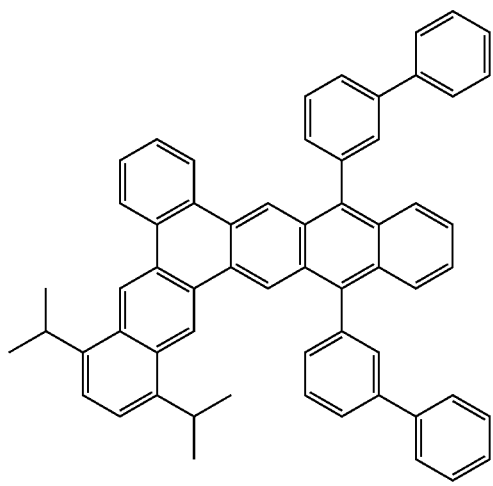
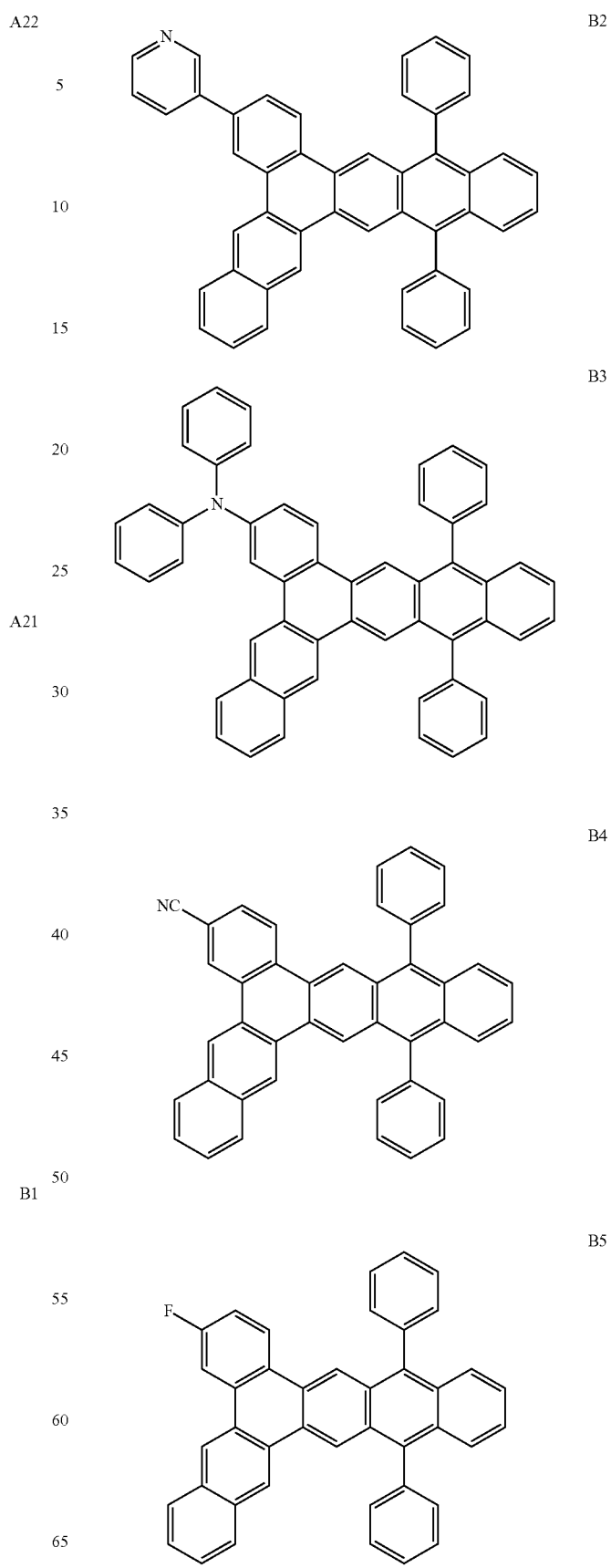

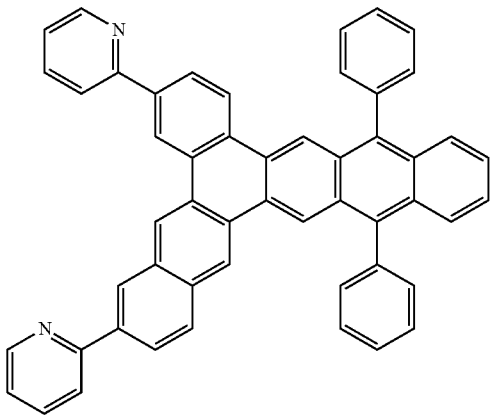

B6

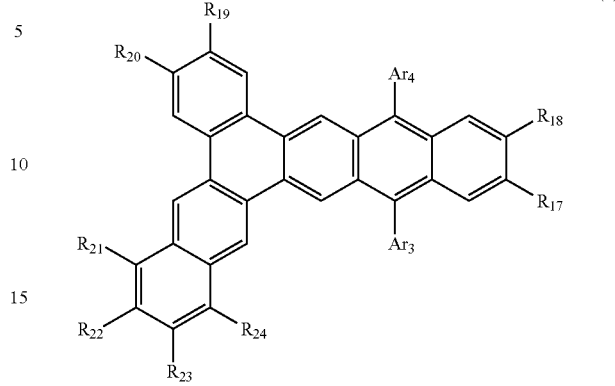

(2)

In Formula (2), $R_{17}$ to $R_{24}$ each independently selected from hydrogen and halogen atoms and methyl, ethyl, iso-propyl, t-butyl, cyano, diphenylamino, pyridyl, phenyl, biphenyl, terphenyl, and naphthyl groups.

The diphenylamino, pyridyl, phenyl, biphenyl, terphenyl, and naphthyl groups optionally have substituents, at least one of methyl, ethyl, iso-propyl, t-butyl, and fluorine groups.

$Ar_3$ and $Ar_4$ are any of phenyl, biphenyl, terphenyl, and naphthyl groups.

$Ar_3$ and $Ar_4$ optionally have substituents, at least one of methyl, ethyl, iso-propyl, t-butyl, and fluorine groups.

Each substituent corresponds to that in Formula (1), and the role and effect thereof are the same as those of the corresponding substituent in Formula (1).

Example compounds belonging to Groups A and B have been described above, but organic compounds according to the present invention are not limited to these example compounds.

The organic compound according to the present invention can be used as a host material of a light-emitting layer of an organic light-emitting device. In such a case, the luminescent color of the organic light-emitting device is not limited to green and red and can be, for example, white or an intermediate color. In addition, the organic compound can be used as a guest material of a light-emitting layer of an organic light-emitting device emitting green light.

Explanation of Synthesis Route

An example of synthesis route of the organic compound according to the present invention will be described with reference to reaction formulae below.

In order to introduce a substituent into a compound in the following formulae, the substituent can be introduced into a desired position by substituting a hydrogen atom at the position by another substituent such as an alkyl group, a hydrogen atom, or a phenyl group.

Synthesis Route 1

Characteristics of Each Exemplified Compound Group

The compounds belonging to group A are each composed of only hydrocarbons over the entire molecule. Compounds composed of only hydrocarbons have low HOMO energy levels. This means that the compounds have low oxidation potentials and are stable against oxidation.

Herein, a low HOMO energy level means that the HOMO energy level is far from the vacuum level and is also expressed as a deep HOMO.

Accordingly, among the organic compounds according to the present invention, the compounds composed of only hydrocarbons belonging to group A have high molecular stability.

The compounds belonging to group B have hetero atoms in substituents. The hetero atoms change the oxidation potential, intermolecular interaction, and also electron-transporting ability of the molecules.

Consequently, the organic compounds can be used as host materials being excellent in adjustment of carrier balance and efficiently generating excitons. The organic compounds can be used, in addition to as the host material, for example, in an electron-transporting layer or electron-injecting layer.

The organic compound according to the present invention can be a compound represented by the following Formula (2):

[Chem. 13]

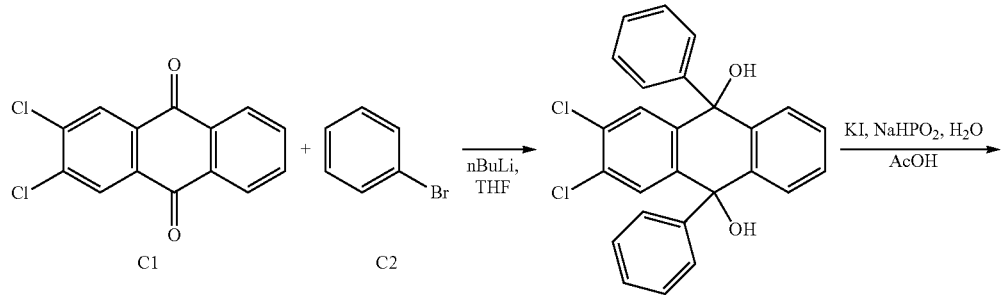

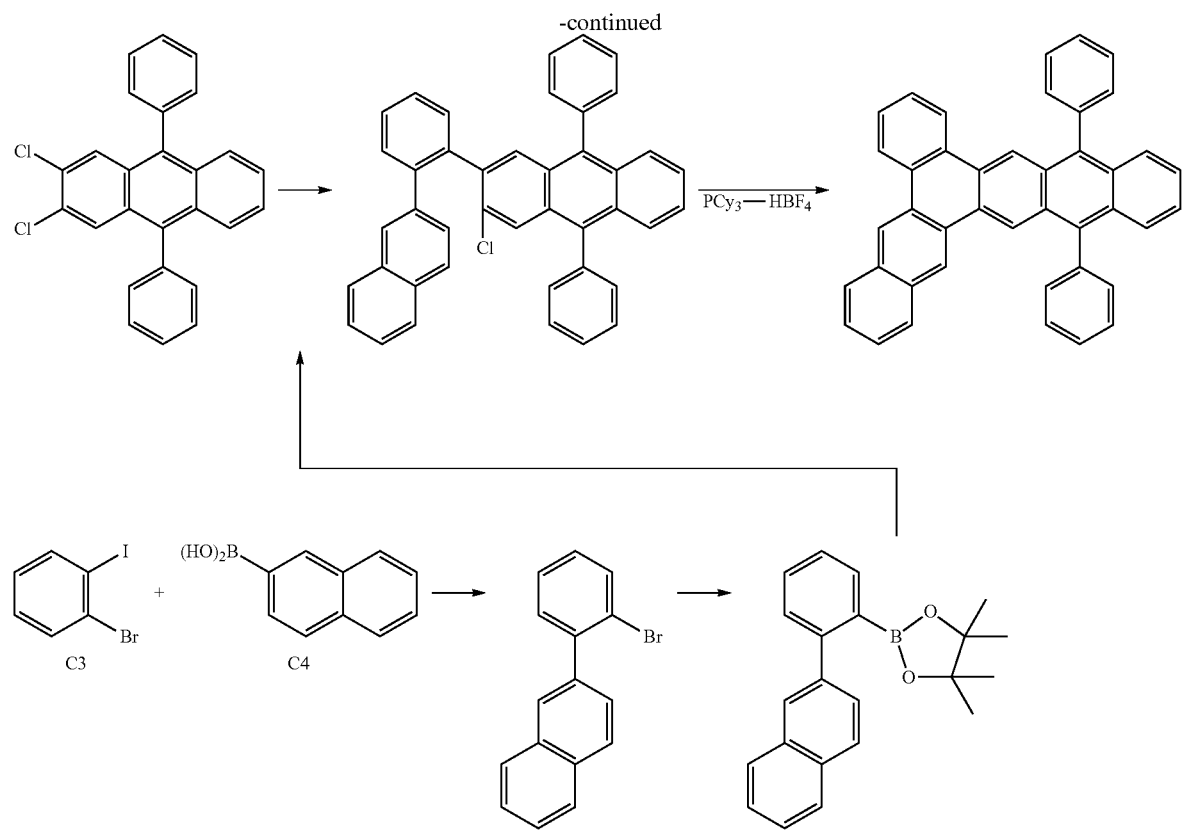
Other Organic Compounds and Raw Materials
Various organic compounds can be synthesized by changing C1 to C4 in the above-mentioned reaction formulae. Specific examples thereof are shown in Table 4 together with the raw materials for synthesizing the compounds.

TABLE 4-continued
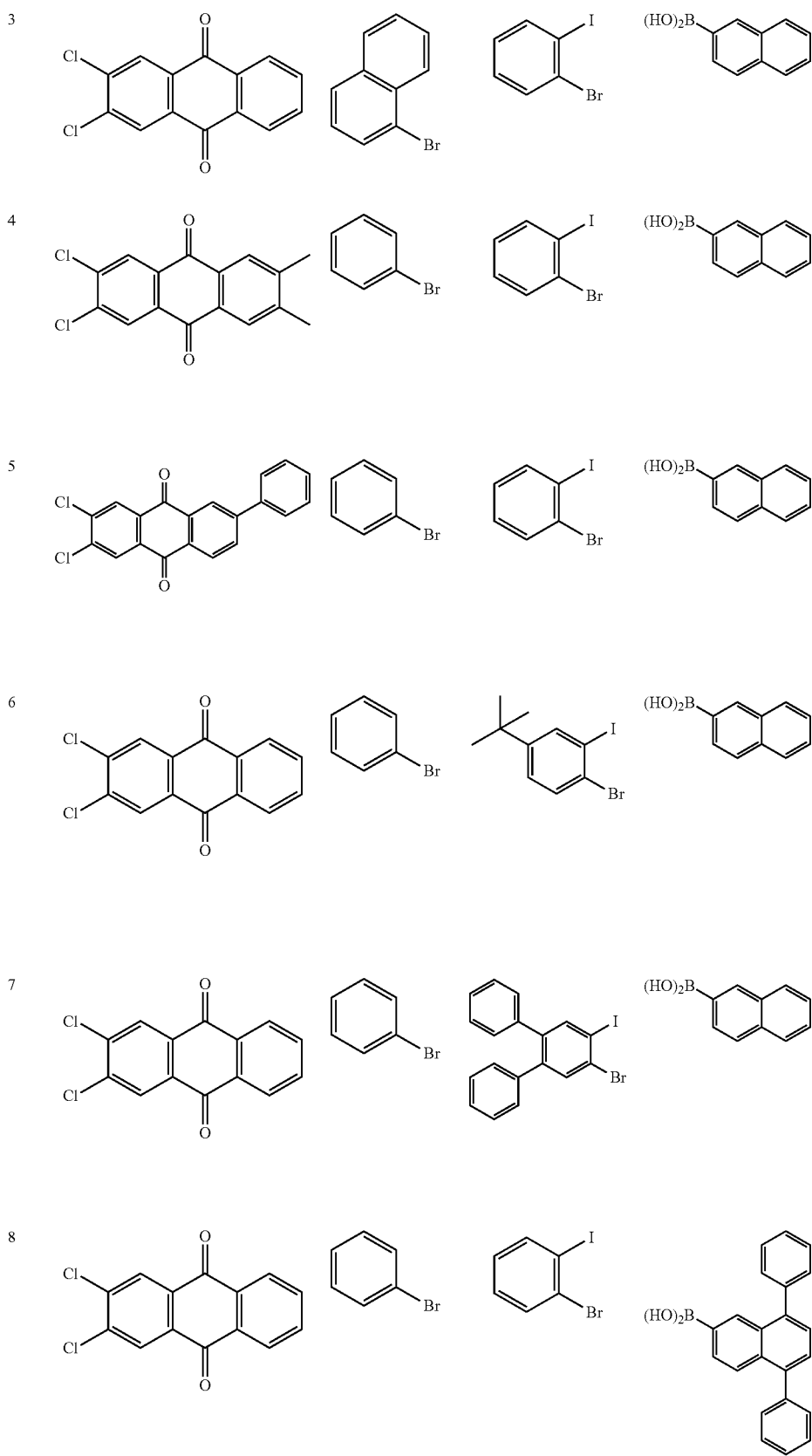

TABLE 4-continued

| Synthesis Example | Synthesized compound | Example Compound No. |
|---|---|---|
| 1 | | A1 |
| 2 | | A4 |
| 3 | | A6 |
| 4 | | A7 |

TABLE 4-continued

| | | |
|---|---|---|
| 5 | 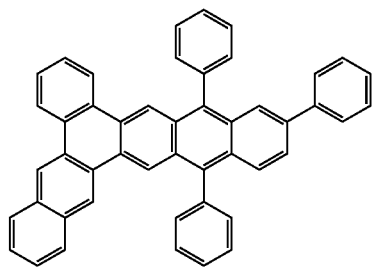 | A9 |
| 6 | 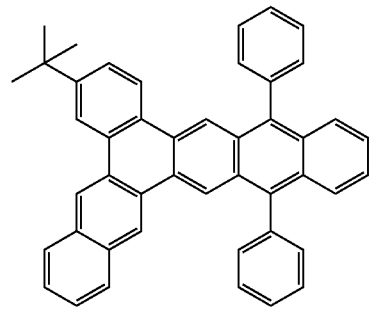 | A10 |
| 7 | 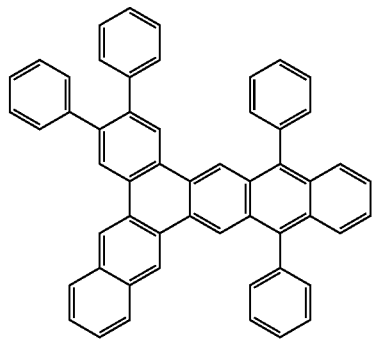 | A11 |
| 8 | 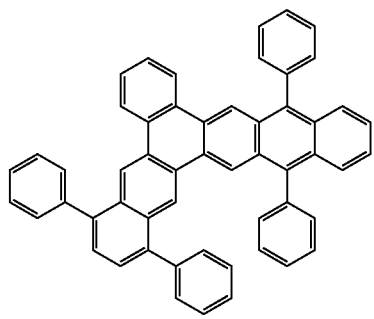 | A15 |

Explanation of Organic Light-Emitting Device According to the Embodiment

An organic light-emitting device according to the embodiment will now be described.

The organic light-emitting device according to this embodiment includes a pair of electrodes, an anode and a cathode, and an organic compound layer disposed therebetween. In this device, the organic compound layer includes the organic compound represented by Formula (1).

The organic compound layer of the organic light-emitting device according to the embodiment may be a monolayer or a multilayer.

Herein, a multilayer includes those appropriately selected from, for example, a hole-injecting layer, a hole-transporting layer, a light-emitting layer, a hole-blocking layer, an electron-transporting layer, an electron-injecting layer, and an exciton-blocking layer. A plurality of layers selected from the above-mentioned layers can be used in combination.

The configuration of the organic light-emitting device according to the embodiment is not limited thereto, and various layer configurations can be employed. For example, an insulating layer may be disposed at the interface between an electrode and an organic compound layer; an adhesive layer or an interference layer may be provided; or an electron-transporting layer or a hole-transporting layer may be composed of two layers having different ionization potentials.

The configuration of the device may be a top emission system, which extracts light from the electrode on the substrate side, or a bottom emission system, which extracts light from the opposite side of the substrate. Alternatively, a configuration in which light is extracted from both sides can also be employed.

In the organic light-emitting device according to the embodiment, the light-emitting layer can contain the organic compound according to the present invention.

The concentration of the host material in the light-emitting layer of the organic light-emitting device according to the embodiment is 50 wt % or more and 99.9 wt % or less, in particular, 80 wt % or more and 99.5 wt % or less, based on the total amount of the light-emitting layer.

The concentration of the guest material in the light-emitting layer of the organic light-emitting device according to the embodiment is 0.01 wt % or more and 30 wt % or less, in particular, 0.1 wt % or more and 20 wt % or less, based on the host material.

The light-emitting layer may be a monolayer or a multilayer. For example, a white-light-emitting device may have any of the light-emitting layer configurations shown below, but the configuration is not limited thereto:

(1) Monolayer: a device containing blue-, green-, and red-light-emitting materials;
(2) Monolayer: a device containing blue- and yellow-light-emitting materials;
(3) Two-layer: a layered device composed of a blue-light-emitting layer and a light-emitting layer containing green- and red-light-emitting materials or composed of a red-light-emitting layer and a light-emitting layer containing blue- and green-light emitting materials;
(4) Two-layer: a layered device composed of a light blue-light-emitting layer and a yellow-light-emitting layer; and
(5) Three-layer: a layered device composed of a blue-light-emitting layer, a green-light-emitting layer, and a red-light-emitting layer.

In the case of that the organic light-emitting device according to the embodiment emits white light, the light-emitting layers emit light of different colors, i.e., red, green, and blue, and white light is emitted by mixing the respective luminescent colors. The material emitting green light can be the organic compound according to the embodiment.

The organic white-light-emitting device according to the embodiment may be of a configuration having a plurality of light-emitting layers or a configuration having a light-emitting portion including a plurality of light-emitting materials.

FIG. 1 is a schematic cross-sectional view illustrating a device configuration having a lamination type light-emitting layer, which is an example of the organic white-light-emitting device according to the embodiment. This figure shows an organic light-emitting device having three light-emitting layers that emit light of different colors. The structure will be described in detail below.

This organic light-emitting device has a device configuration where an anode 1, a hole-injecting layer 2, a hole-transporting layer 3, a blue-light-emitting layer 4, a green-light-emitting layer 5, a red-light-emitting layer 6, an electron-transporting layer 7, an electron-injecting layer 8, and a cathode 9 are laminated on a substrate such as a glass substrate. The order of the lamination of the blue-, green-, and red-light-emitting layers may be changed.

The configuration of the light-emitting layers is not limited to lamination, and the layers may be horizontally arranged. In the horizontal arrangement, every light-emitting layer is in contact with the adjacent layers such as a hole-transporting layer and an electron-transporting layer.

The light-emitting layer may have a configuration where a single light-emitting layer contains light-emitting materials emitting light of different colors. In such a case, the light-emitting materials form the respective domains.

In the white-light-emitting device according to the embodiment, the light-emitting materials of the blue-light-emitting layer, the green-light-emitting layer, and the red-light-emitting layer are not particularly limited. For example, compounds having a chrysene skeleton, a fluoranthene skeleton, or an anthracene skeleton; boron complexes; or iridium complexes can be used.

The white color according to the embodiment includes pure white and neutral white color. The white color according to the embodiment has a color temperature of 3000 to 9500 K. The emission of the organic white-light-emitting device according to the embodiment has C.I.E. chromaticity coordinates of x in the range of 0.25 to 0.50 and y in the range of 0.30 to 0.42.

In the organic light-emitting device according to the present invention, in addition to the compound according to the present invention, for example, a known hole-injecting material, hole-transporting material, host material, guest material, electron-injecting material, or electron-transporting material can be optionally used. These materials may be a low-molecular compound or a high-molecular compound.

Examples of these compounds will be shown below.

As the hole-injecting or transporting material, a material having high hole mobility can be used. Examples of the low- or high-molecular material having hole-injecting or transporting ability include, but not limited to, triarylamine derivatives, phenylenediamine derivatives, stilbene derivatives, phthalocyanine derivatives, porphyrin derivatives, poly(vinylcarbazole), poly(thiophene), and other electrically conductive polymers.

Examples of the host material include, but not limited to, triarylamine derivatives, phenylene derivatives, fused ring aromatic compounds (e.g., naphthalene derivatives, phenanthrene derivatives, fluorene derivatives, and chrysene derivatives), organic metal complexes (e.g., organic aluminum complexes such as tris(8-quinolinolate)aluminum, organic beryllium complexes, organic iridium complexes, and organic platinum complexes), and polymer derivatives such as poly(phenylenevinylene) derivatives, poly(fluorene) derivatives, poly(phenylene) derivatives, poly(thienylenevinylene) derivatives, and poly(acetylene) derivatives.

Specific structural formulae of the guest compound are shown in Table 5. The derivatives of the compounds having the structural formulae shown in Table 5 also can be used as the guest compound. Other examples of the guest compound include, but not limited to, fused ring compounds (e.g., fluorene derivatives, naphthalene derivatives, anthracene derivatives, pyrene derivatives, benzofluoranthene derivatives, carbazole derivatives, quinoxaline derivatives, and quinoline derivatives), organic zinc complexes, triphenylamine derivatives, and polymer derivatives such as poly(fluorene) derivatives and poly(phenylene) derivatives.

Among the above-mentioned guest compounds, in particular, anthracene derivatives and fluoranthene derivatives can be used.

The anthracene derivatives have a structure composed of three linearly fused six-membered aromatic rings and include the structure shown as D3 in Table 5. As the anthracene derivatives, compounds having anthracene as the basic skeleton and, in particular, having substituents at 9- and 10-positions can be used.

The benzofluoranthene derivatives have benzofluoranthene in the basic skeleton. The benzofluoranthene may have fused rings as in D1 to D3. Among the benzofluoranthene derivatives, in particular, benzo[k]fluoranthene can be used.

TABLE 5
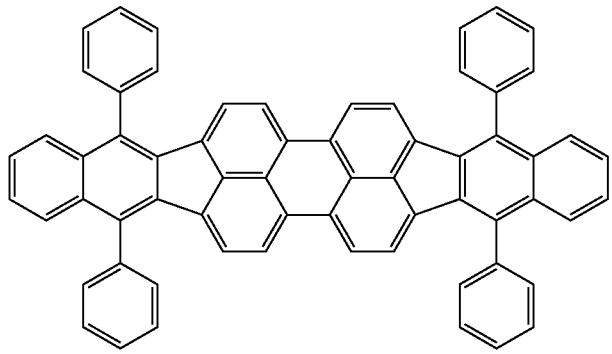 [SMILES: c1ccc(-c2c3c(c(-c4ccccc4)c4ccccc24)-c2ccc4c5ccc6c7c(ccc(c8ccc-3c2c84)c75)-c2c-6c(-c3ccccc3)c3ccccc3c2-c2ccccc2)cc1]
D1
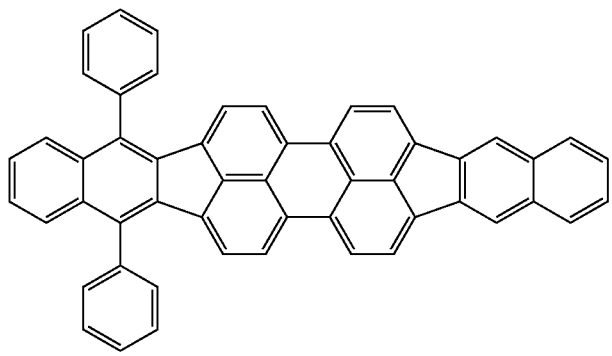 [SMILES: c1ccc(-c2c3c(c(-c4ccccc4)c4ccccc24)-c2ccc4c5ccc6c7c(ccc(c8ccc-3c2c84)c75)-c2cc3ccccc3cc2-6)cc1]
D2
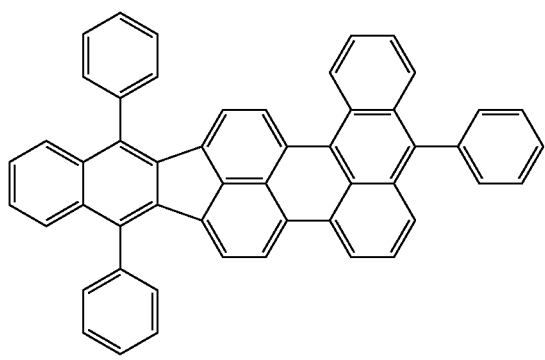 [SMILES: c1ccc(-c2c3c(c(-c4ccccc4)c4ccccc24)-c2ccc4c5c2c-3ccc5c2cccc3c(-c5ccccc5)c5ccccc5c4c32)cc1]
D3
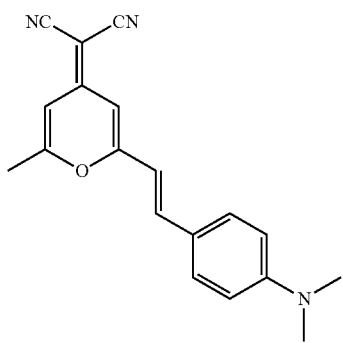
D4

TABLE 5-continued
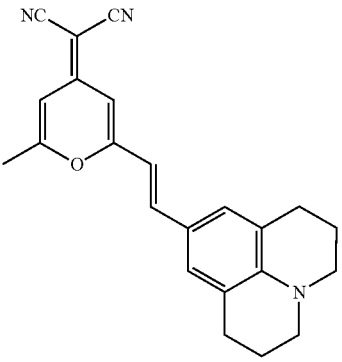 [SMILES: CC1=CC(=C(C#N)C#N)C=C(/C=C/c2cc3c4c(c2)CCCN4CCC3)O1]
D5
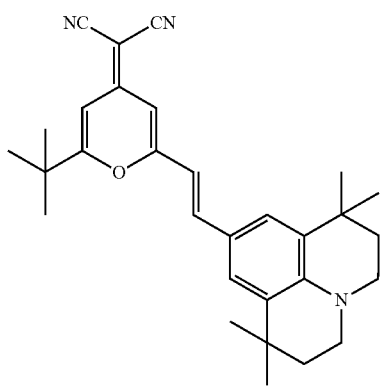 [SMILES: CC(C)(C)C1=CC(=C(C#N)C#N)C=C(/C=C/c2cc3c4c(c2)C(C)(C)CCN4CCC3(C)C)O1]
D6
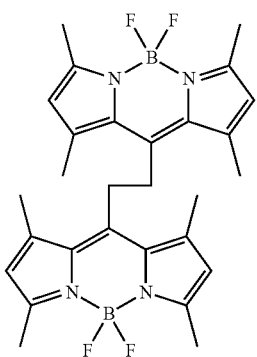
D7
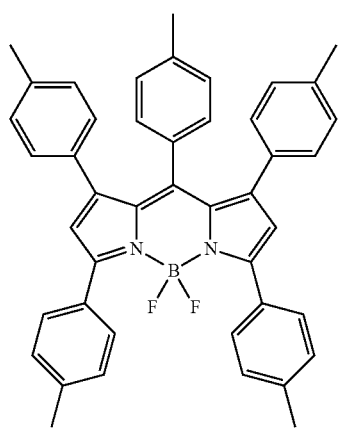
D8

TABLE 5-continued

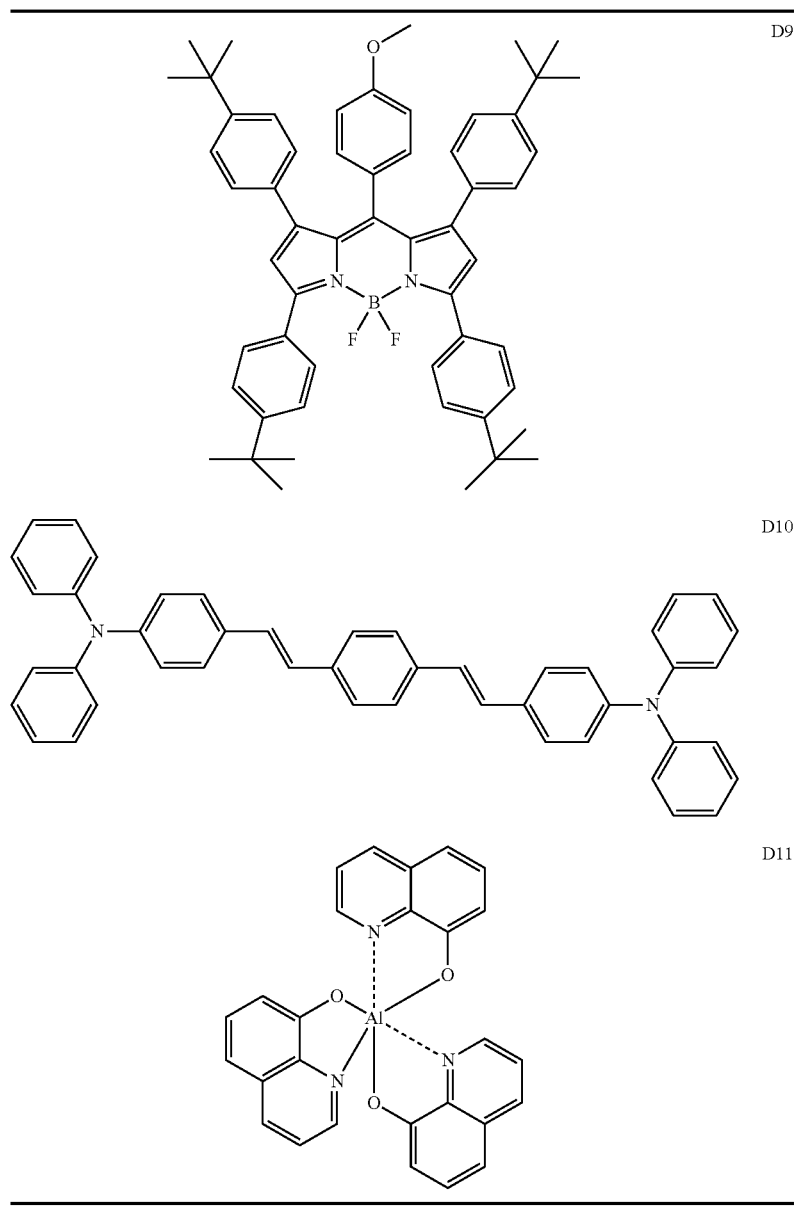

The electron-injecting or transporting material is appropriately selected by considering, for example, the balance with the hole mobility of the hole-injecting or transporting material. Examples of the material having electron-injecting or transporting ability include, but not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes.

As the anode material, a material having a higher work function is used. Examples of the material include simple metals such as gold, platinum, silver, copper, nickel, palladium, cobalt, selenium, vanadium, and tungsten; alloys of these simple metals; and metal oxides such as tin oxide, zinc oxide, indium oxide, indium tin oxide (ITO), and indium zinc oxide. In addition, electrically conductive polymers such as polyaniline, polypyrrole, and polythiophene can be used.

These electrode materials may be used alone or in combination. The anode may have a monolayer structure or a multilayer structure.

In contrast, as the cathode material, a material having a lower work function is used. Examples of the material include alkali metals such as lithium; alkaline earth metals such as calcium; simple metals such as aluminum, titanium, manganese, silver, lead, and chromium; and alloys of these simple metals, such as magnesium-silver, aluminum-lithium, and aluminum-magnesium. In addition, metal oxides such as indium tin oxide (ITO) can be used. These electrode materials may be used alone or in combination. The cathode may have a monolayer structure or a multilayer structure.

In the organic light-emitting device according to the embodiment, a layer containing the fused multi-ring compound according to the embodiment and layers of other organic compounds are formed by the following methods:

For example, a layer is formed by vacuum vapor deposition, ionized vapor deposition, sputtering, plasma coating, or known coating such as spin coating, dipping, a casting method, an LB method, or an ink-jetting method of a compound dissolved in an appropriate solvent.

In the case of forming a layer by vacuum deposition, solution coating, or the like, crystallization hardly occurs, and the resulting layer shows excellent stability for a long time. In addition, in coating, a film can be formed in combination with an appropriate binder resin.

Examples of the binder resin include, but not limited to, polyvinyl carbazole resins, polycarbonate resins, polyester resins, ABS resins, acrylic resins, polyimide resins, phenol resins, epoxy resins, silicone resins, and urea resins.

These binder resins may be used alone as a homopolymer or a copolymer or in combination of two or more thereof. In addition, known additives such as a plasticizer, an antioxidant, and a UV absorber may be optionally used together with the resin binder.

Use of Organic Light-Emitting Device According to the Embodiment

The organic light-emitting device according to the embodiment can be used as a component of a display apparatus or a lighting system. Other examples of use include exposure light sources of electrophotographic image forming apparatuses, backlights of liquid crystal display apparatuses, and white light sources. The organic light-emitting device may further include a color filter.

The display apparatus includes the organic light-emitting device according to the embodiment in a display section. This display section includes a plurality of pixels, and the pixels each include the organic light-emitting device according to the embodiment and an active device connected to the organic light-emitting device.

An example of the active device is a switching device for controlling luminance. An example of the switching device is a TFT device. The anode or the cathode of the organic light-emitting device is connected to the drain electrode or the source electrode of the TFT device. Here, the display apparatus can be used as an image display apparatus of, for example, a PC.

The display apparatus may be an image display apparatus that includes an image input section for inputting image information from, for example, an area CCD, a linear CCD, or a memory card and displays the input image on the display section.

The display section of an image pickup apparatus or ink-jet printer may have an image-outputting function for displaying image information input from the outside and an inputting function as an operating panel for inputting information to be processed into an image. The display apparatus may be used in the display section of a multi-functional printer.

The lighting system is an apparatus for lighting, for example, a room. The lighting system may emit light of white, neutral white, or any color from blue to red. The lighting system includes the organic light-emitting device according to the embodiment and a converter circuit connected to the device. The white color has a color temperature of about 4200 K, and the neutral white color has a color temperature of about 5000 K. The lighting system may have a color filter.

The AC/DC converter circuit according to the embodiment converts AC voltage to DC voltage.

The organic light-emitting device according to the embodiment can be used in an exposure unit of an image-forming apparatus.

The image-forming apparatus includes a photosensitive member, a charging unit for charging a surface of the photosensitive member, an exposure unit for forming an electrostatic latent image by exposing the photosensitive member, and a developing unit for developing the electrostatic latent image formed on the surface of the photosensitive member.

A display apparatus including the organic light-emitting device according to the embodiment will now be described with reference to FIG. 2.

Figure 2:
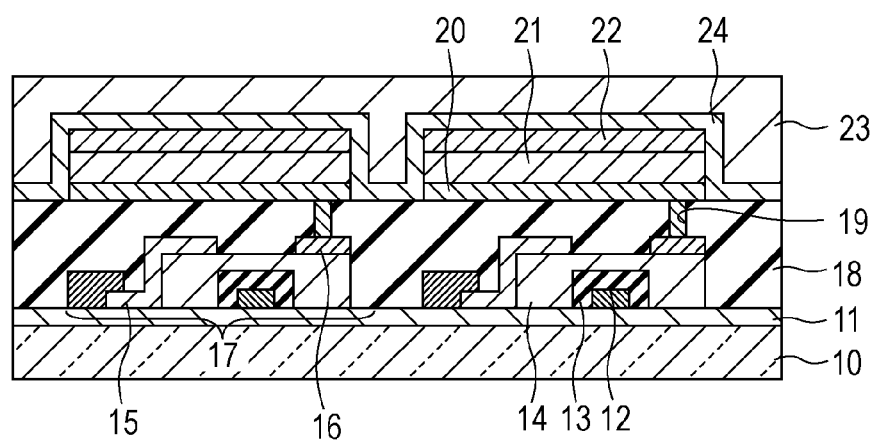
FIG. 2 is a schematic cross-sectional view illustrating organic light-emitting devices according to the embodiment and switching devices connected to the organic light-emitting devices.

FIG. 2 is a schematic cross-sectional view of a display apparatus having organic light-emitting devices according to the embodiment and TFT devices connected to the organic light-emitting devices.

The display apparatus includes a substrate 10 such as a glass substrate and a moisture-proof film 11 disposed on the substrate 10 for protecting the TFT devices or the organic compound layer. Reference numeral 12 denotes a metal gate electrode, reference numeral 13 denotes a gate insulating film, and reference numeral 14 denotes a semiconductor layer.

The TFT device 17 includes a semiconductor layer 14, a drain electrode 15, and a source electrode 16. An insulating film 18 is disposed on the TFT device 17. The anode 20 of the organic light-emitting device and the source electrode 16 are connected to each other via a contact hole 19.

The display apparatus according to the embodiment is not limited to this configuration as long as either the anode or the cathode is connected to either the source electrode or the drain electrode of the TFT device.

In FIG. 2, the organic compound layer 21 of a multilayer is shown as one layer. The organic compound layer may be a monolayer or a multilayer. Furthermore, a first protective layer 23 and a second protective layer 24 are disposed on the cathode 22 to prevent the organic light-emitting device from deteriorating.

When the display apparatus according to the embodiment emits white light, for example, the lamination type light-emitting layer shown in FIG. 1 is used as the organic compound layer 21 in FIG. 2.

The light-emitting layers of the display apparatus that emits white light according to the embodiment are not limited to the device configuration shown in FIG. 1. The light-emitting layers that emit light of different colors may be horizontally arranged, or materials emitting light of different colors may form the respective domains in a single light-emitting layer.

In the organic light-emitting device according to the embodiment, the TFT device as an example of switching device controls the luminance. Organic light-emitting devices disposed in a plurality of planes can display images with the respective luminance.

The switching device of the organic light-emitting device according to the embodiment is not limited to the TFT device and may be a transistor, an MIM device, or an active matrix driver directly formed on a substrate such as a Si substrate. Direct formation on a substrate is also expressed as formation in a substrate.

These configurations are selected depending on the resolution. For example, in a resolution of about 1-inch QVGA, the organic light-emitting devices can be disposed on a Si substrate.

It is possible to stably display an image with high quality for a long time by driving a display apparatus including the organic light-emitting devices according to the embodiment.

EXAMPLES

Example 1

Synthesis of Example Compound A1

[Chem. 14]

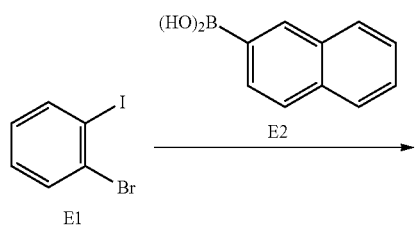

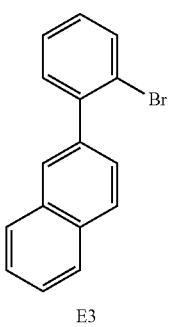

A 500-mL recovery flask was charged with 6.00 g (21.2 mmol) of compound E1, 3.84 g (22.3 mmol) of compound E2, 735 mg of Pd(PPh$_3$)$_4$, 100 mL of toluene, 50 mL of ethanol, and 100 mL of 2 M sodium carbonate aqueous solution, followed by stirring at 90° C. for 8 hours under a nitrogen gas flow.

After completion of the reaction, water and toluene were added to this reaction solution. Subsequently, the organic layer was recovered by solvent extraction operation and dried over sodium sulfate.

The solvent was removed from the organic layer by distillation under reduced pressure, and the resulting residue was purified by silica gel column chromatography (mobile phase: chloroform:heptane=1:3) to give 5.22 g (yield: 87%) of compound E3 as a colorless transparent liquid.

[Chem. 15]

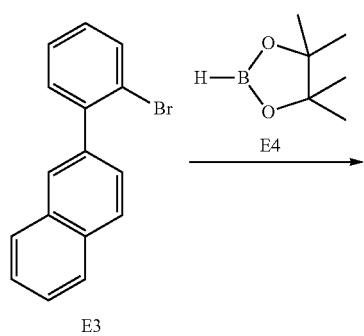

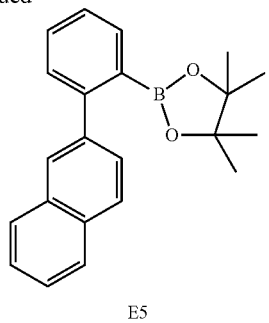

A 200-mL recovery flask was charged with 2.60 g (9.18 mmol) of compound E3, 3.53 g (27.5 mmol) of compound E4, 2.79 mg (27.5 mmol) of triethylamine, 498 mg of Ni(dppp)Cl$_2$, and 30 mL of toluene, followed by stirring at 95° C. for 5 hours under a nitrogen gas flow.

After completion of the reaction, water and toluene were added to this reaction solution. Subsequently, the organic layer was recovered by solvent extraction operation and dried over sodium sulfate.

The solvent was removed from the organic layer by distillation under reduced pressure, and the resulting residue was purified by silica gel column chromatography (mobile phase: toluene:heptane=1:1) to give 1.70 g (yield: 56%) of compound E5 as a white solid.

[Chem. 16]

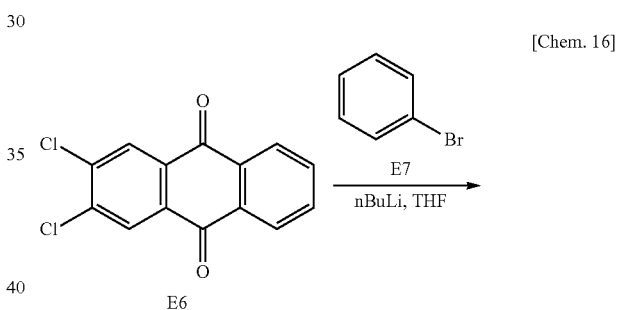

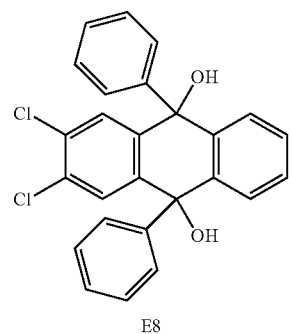

A 200-mL recovery flask was charged with 6.47 g (41.2 mmol) of compound E7 and a THF solution, followed by stirring at −78° C. for 1 hour under a nitrogen gas flow. To this solution, 25.8 mL (41.2 mmol) of a 1.6 M nBuLi-hexane solution was gradually added at −78° C., followed by stirring for 1 hour under a nitrogen gas flow.

Subsequently, 4.56 g (16.5 mmol) of compound E6 was added to the reaction solution, followed by stirring at room temperature overnight under a nitrogen gas flow. After completion of the reaction, water and dichloromethane were added to this reaction solution. Subsequently, the organic layer was recovered by solvent extraction operation and dried over sodium sulfate.

The solvent was removed from the organic layer by distillation under reduced pressure, and the resulting residue was washed by dispersing in a solvent mixture of chloroform and heptane to give 5.85 g (yield: 82%) of compound E8 as a white solid.

[Chem. 17]

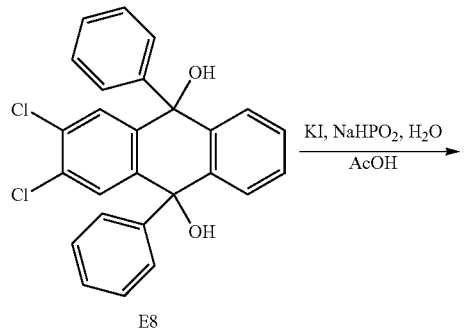

E8

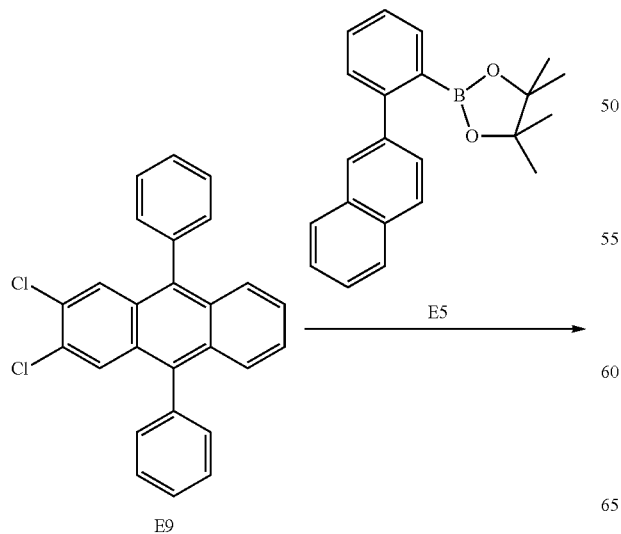

E9

A 200-mL recovery flask was charged with 4.58 g (10.5 mmol) of compound E8, 2.10 g (12.7 mmol) of potassium iodide, 1.34 g (12.7 mmol) of $NaH_2PO_2 \cdot H_2O$, and 90 mL of acetic acid, followed by stirring at 100° C. for 1 hour under a nitrogen gas flow.

After completion of the reaction, water was added to this reaction solution, and the precipitate was recovered. Subsequently, the precipitate was washed by dispersing in methanol to give a crude product. The resulting crude product was purified by silica gel column chromatography (mobile phase: toluene:heptane=1:1) to give 2.88 g (yield: 68%) of compound E9 as a light yellow solid.

[Chem. 18]

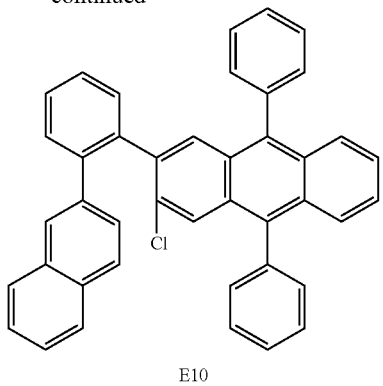

E10

A 200-mL recovery flask was charged with 695 mg (2.11 mmol) of compound E5, 700 mg (1.75 mmol) of compound E9, 291 mg (0.71 mmol) of 2-dicyclohexylphosphino-2',6'-dimethoxybiphenyl, 121 mg (0.21 mmol) of $Pd(dba)_2$, 928 mg (4.38 mmol) of $K_3PO_4$, and 30 mL of toluene, followed by stirring at 100° C. for 3 hours under a nitrogen gas flow.

After completion of the reaction, water and toluene were added to this reaction solution. Subsequently, the organic layer was recovered by solvent extraction operation and dried over sodium sulfate.

The solvent was removed from the organic layer by distillation under reduced pressure, and the resulting residue was purified by silica gel column chromatography (mobile phase: chloroform:heptane=1:3) to give 810 mg (yield: 82%) of compound E10 as a light yellow solid.

[Chem. 19]

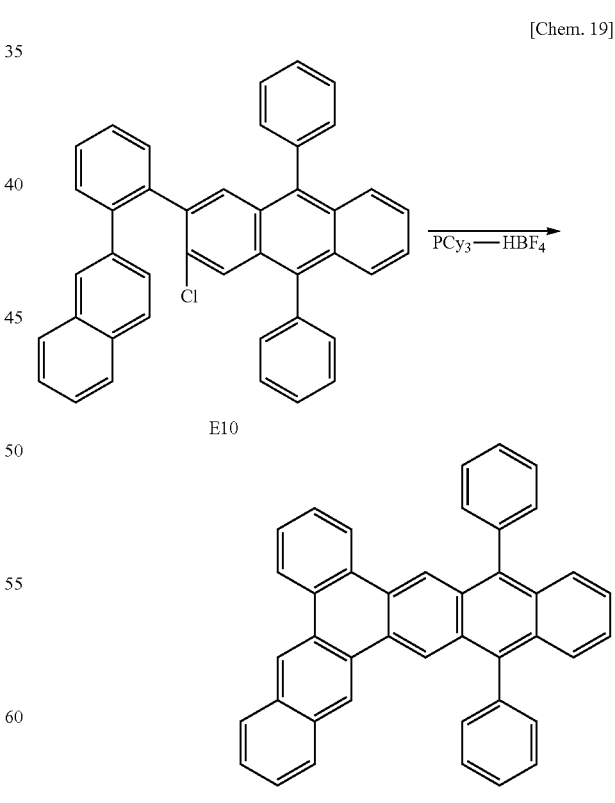

A 50-mL of recovery flask was charged with 820 mg (1.44 mmol) of compound E10, 40 mg (0.17 mmol) of palladium acetate, 128 mg (0.35 mmol) of PCy3-HBF4, 497 mg (3.60 mmol) of potassium carbonate, and 10 mL of N,N-dimethylacetamide, followed by stirring at 140° C. for 4 hours under a nitrogen gas flow.

After completion of the reaction, water and toluene were added to this reaction solution. Subsequently, the organic layer was recovered by solvent extraction operation and dried over sodium sulfate.

The solvent was removed from the organic layer by distillation under reduced pressure, and the resulting residue was purified by silica gel column chromatography (mobile phase: chloroform:heptane=1:3) to give 427 mg (yield: 56%) of Example Compound A1 as a yellow solid.

Four hundred milligrams of the resulting Example Compound A1 was subjected to sublimation purification at a degree of vacuum of $7.0 \times 10^{-1}$ Pa, an argon gas flow of 10 mL/min, and a sublimation temperature of 320° C. with a sublimation purification apparatus manufactured by Ulvac Kiko Inc. to give 370 mg of highly purified Example Compound A1.

The prepared compound was identified by mass spectrometry.

Matrix-assisted laser desorption ionization time-of-flight mass spectrometry (MALDI-TOF-MS):
Observed value: m/z=530.52, calculated value: $C_{42}H_{26}O$=530.66.

The energy gap of Example Compound A1 was measured by the following process.

Example Compound A1 was vapor-deposited on a glass substrate to form a vapor-deposited thin film with a thickness of 20 nm. The absorption spectrum of this vapor-deposited thin film was measured with an ultraviolet and visible spectrophotometer (V-560, manufactured by JASCO Corp.). The energy gap of Example Compound A1 was determined to be 2.5 eV from the absorption edge of the resulting absorption spectrum.

Example 2

Synthesis of Example Compound A4

Example Compound A4 was prepared by the same reaction and purification processes as in Example 1 except that organic compound E11 was used instead of organic compound E7 in Example 1.

[Chem. 20]

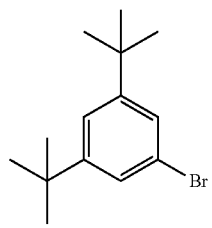

E11

The prepared compound was identified by mass spectrometry.
MALDI-TOF-MS:
Observed value: m/z=755.58, calculated value: $C_{58}H_{58}$=755.08.

The energy gap of Example Compound A4 measured as in Example 1 was 2.3 eV.

Example 3

Synthesis of Example Compound A6

Example Compound A6 was prepared by the same reaction and purification processes as in Example 1 except that organic compound E12 was used instead of organic compound E7 in Example 1.

[Chem. 21]

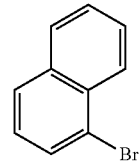

E12

The prepared compound was identified by mass spectrometry.
MALDI-TOF-MS:
Observed value: m/z=630.22, calculated value: $C_{50}H_{30}$=630.77.

The energy gap of Example Compound A6 measured as in Example 1 was 2.6 eV.

Example 4

Synthesis of Example Compound A10

Example Compound A10 was prepared by the same reaction and purification processes as in Example 1 except that organic compound E13 was used instead of organic compound E1 in Example 1.

[Chem. 22]

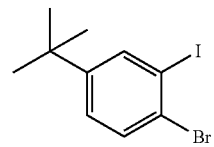

E13

The prepared compound was identified by mass spectrometry.
MALDI-TOF-MS:
Observed value: m/z=586.20, calculated value: $C_{46}H_{34}$=586.76.

The energy gap of Example Compound A10 measured as in Example 1 was 2.5 eV.

Example 5

Synthesis of Example Compound A15

Example Compound A15 was prepared by the same reaction and purification processes as in Example 1 except that organic compound E14 was used instead of organic compound E2 in Example 1.

[Chem. 23]

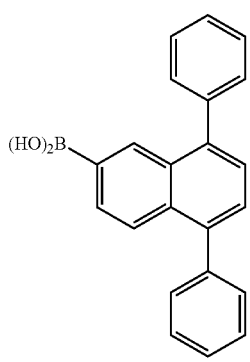

E14

The prepared compound was identified by mass spectrometry.

MALDI-TOF-MS:
Observed value: m/z=682.52, calculated value: $C_{54}H_{34}$=682.85.

The energy gap of Example Compound A15 measured as in Example 1 was 2.5 eV.

Comparative Example 1

Synthesis of Comparative Compound (2)

Comparative Compound (2) was prepared by the same reaction and purification processes as in Example 1 except that organic compound E15 was used instead of organic compound E2 in Example 1.

[Chem. 24]

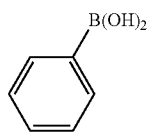

E15

Comparative Example 2

Synthesis of Comparative Compound (3)

Comparative Compound (3) was prepared by the same reaction and purification processes as in Example 1 except that organic compound E16 was used instead of organic compound E9 in Example 1.

[Chem. 25]

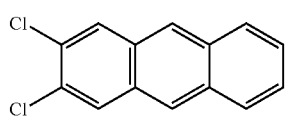

E16

In this example, a multilayered-type organic light-emitting device (anode/hole-injecting layer/hole-transporting layer/light-emitting layer/electron-transporting layer/electron-injecting layer/cathode) was produced: ITO with a thickness of 100 nm was patterned on a glass substrate. On the resulting ITO substrate, the following organic layers and electrodes were sequentially formed by resistance heating vacuum vapor deposition in a vacuum chamber of $10^{-5}$ Pa such that the facing area of the electrodes is 3 mm². The structure of compound D1 is shown in Table 5.

Hole-injecting layer (30 nm): compound F1

Hole-transporting layer (10 nm): compound F2

Light-emitting layer (30 nm): host: compound A1 (weight ratio: 99.5%), guest: compound D1 (weight ratio: 0.5%)

Electron-transporting layer (30 nm): compound F4

Electron-injecting layer (1 nm): LiF

Metal electrode layer (100 nm): Al

[Chem. 26]

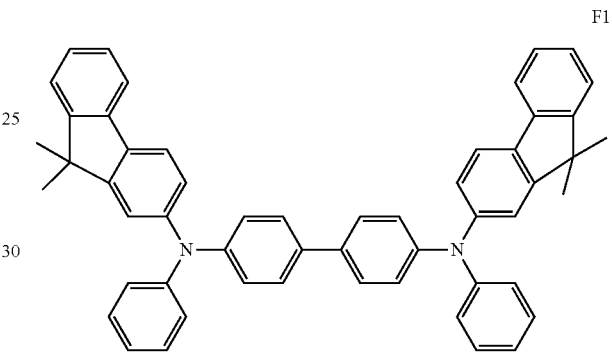

F1

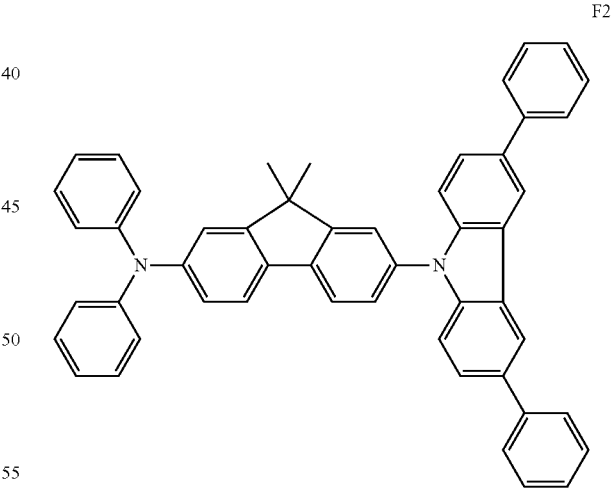

F2

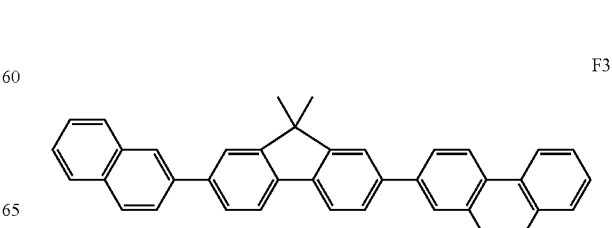

F3

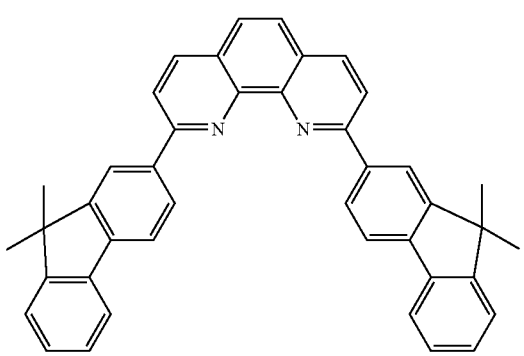

A voltage of 5.2 V was applied to the resulting organic light-emitting device using the ITO electrode as the positive electrode and the Al electrode as the negative electrode to observe red light emission with a luminous efficiency of 4.8 cd/A and a luminance of 2000 cd/m².

In order to evaluate the stability of the resulting device, the time till the luminance decreases by 10% in driving at an initial luminance of 4500 cd/m² was measured and was confirmed to exceed 70000 hours.

Examples 7 to 10 and Comparative Examples 3 and 4

Devices were produced as in Example 6 except that the host materials and the guest materials in light-emitting layers were changed to those shown in Table 6. The resulting devices were evaluated as in Example 6. The results are shown in Table 6.

TABLE 6

| | Host | Guest | Luminous efficiency (cd/A) | Voltage (V) | Luminescent color | Lifetime for 10% reduction (hr) |
|---|---|---|---|---|---|---|
| Example 7 | A4 | D1 | 5.8 | 5.0 | Red | 26000 |
| Example 8 | A6 | D2 | 5.5 | 5.1 | Red | 20000 |
| Example 9 | A10 | D1 | 5.7 | 4.9 | Red | 25000 |
| Example 10 | A17 | D1 | 5.6 | 5.1 | Red | 20000 |
| Example 11 | A1 | D10 | 5.1 | 4.9 | Green | 10000 |
| Comparative Example 3 | Compound (2) | D1 | 5.2 | 5.2 | Red | 7000 |
| Comparative Example 4 | Compound (3) | D1 | 2.8 | 5.0 | Red | 11000 |

Example 11

In this example, an organic light-emitting device having a resonance structure was produced by the following process:

An aluminum alloy (AlNd) film serving as a reflective anode was formed on a support of a glass substrate by sputtering so as to have a thickness of 100 nm.

Then, an ITO film serving as a transparent anode was formed thereon by sputtering so as to have a thickness of 80 nm. Furthermore, a device isolation film of polyimide having a thickness of 1.5 μm was formed at the peripheral region of the anode, and an opening having a radius of 3 mm was formed. The resulting product was washed by ultrasonic cleaning with acetone and then isopropyl alcohol (IPA) and then washed by boiling in IPA, followed by drying. Furthermore, the surface of this substrate was washed with UV.

Furthermore, organic layers shown below were sequentially formed by vacuum deposition by resistance heating vacuum vapor deposition in a vacuum chamber of $10^{-5}$ Pa, and then a transparent electrode having a thickness of 30 nm was formed as a cathode by sputtering IZO. After the formation, sealing was performed in a nitrogen atmosphere. Thus, an organic light-emitting device was formed.

Hole-injecting layer (185 nm): compound F1
Hole-transporting layer (10 nm): compound F2
Light-emitting layer (35 nm): host: compound A1 (weight ratio: 99.5%), guest: compound D1 (weight ratio: 0.5%)
Electron-transporting layer (10 nm): compound F3
Electron-injecting layer (70 nm): compound F4 (weight ratio: 80%), Li (weight ratio: 20%)

A voltage of 4.6 V was applied to the resulting organic light-emitting device using the ITO electrode as the positive electrode and the IZO electrode as the negative electrode to observe red light emission with a luminous efficiency of 10.6 cd/A and a luminance of 2000 cd/m².

Example 12

In this example, an organic white-light-emitting device having a configuration composed of anode/hole-injecting layer/hole-transporting layer/red-light-emitting layer/green-light-emitting layer/blue-light-emitting layer/electron-transporting layer/electron-injecting layer/cathode disposed in this order on a substrate was produced by the following process:

A film of ITO serving as an anode was formed on a glass substrate by sputtering so as to have a thickness of 120 nm, and the resulting product was used as a transparent electrically conductive support substrate (ITO substrate).

On this ITO substrate, organic compound layers and electrode layers shown below were sequentially formed by resistance heating vacuum vapor deposition in a vacuum chamber of $10^{-5}$ Pa. On this occasion, the area of electrodes facing each other was adjusted to be 3 mm².

Hole-injecting layer (30 nm): compound F1
Hole-transporting layer (10 nm): compound F2
Red-light-emitting layer (15 nm): host 1: compound A1 (weight ratio: 98.5%), host 2: compound F6 (weight ratio: 1.0%), guest: compound D1 (weight ratio: 0.5%)
Green-light-emitting layer (5 nm): host: compound F4 (weight ratio: 95.0%), guest: compound D10 (weight ratio: 5.0%)
Blue-light-emitting layer (20 nm): host: compound F4 (weight ratio: 95.0%), guest: compound F5 (weight ratio: 5.0%)
Electron-transporting layer (30 nm): compound F3
Electron-injecting layer (1 nm): LiF
Metal electrode layer (100 nm): Al

[Chem. 27]

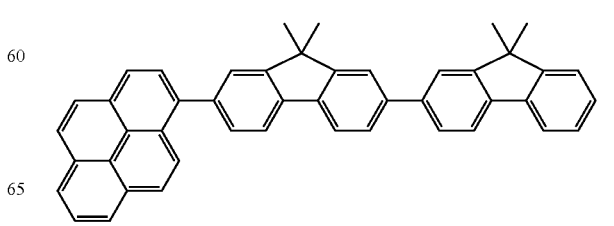

F4

-continued

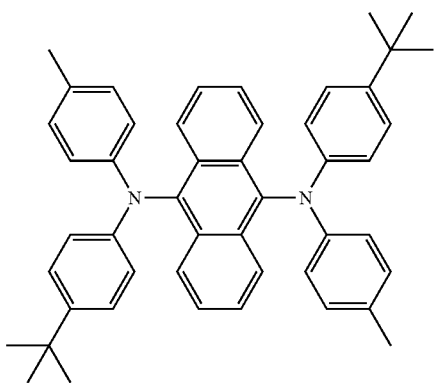

F5

A voltage was applied to the resulting organic light-emitting device using the ITO electrode as the positive electrode and the Al electrode as the negative electrode to observe white light emission with C.I.E. chromaticity coordinates of (0.32, 0.35).

RESULTS AND CONCLUSION

As described above, an organic red-light-emitting device with a long lifetime can be provided by using a novel fused ring compound according to the present invention as a host material in the light-emitting layer. In addition, a white-light-emitting device can be provided by using the fused ring compound together with materials that emit light of other colors.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-227974, filed Oct. 17, 2011, which is hereby incorporated by reference herein in its entirety.

REFERENCE SIGNS LIST 4 blue-light-emitting layer
5 green-light-emitting layer
6 red-light-emitting layer
17 TFT device
20 anode
21 organic compound layer
22 cathode

The invention claimed is:
1. A benzo[h]hexaphene represented by the following Formula (1):

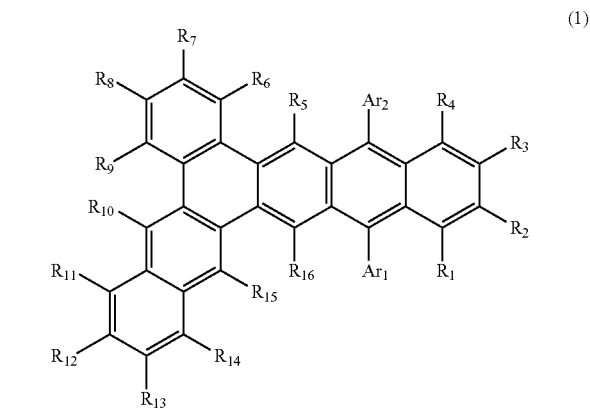

(1)

wherein,
$R_1$ to $R_{16}$ are each independently selected from a hydrogen atom, a halogen atom, a methyl group, an ethyl group, an iso-propyl group, a t-butyl group, a cyano group, a diphenylamino group, a pyridyl group, a phenyl group, a biphenyl group, a terphenyl group, and a naphthyl group;
the diphenylamino, pyridyl, phenyl, biphenyl, terphenyl, and naphthyl groups optionally have a substitutent of a methyl group, an ethyl group, an iso-propyl group, a t-butyl group, or a fluorine atom;
$Ar_1$ and $Ar_2$ are any of a phenyl group, a biphenyl group, a terphenyl group, and a naphthyl group; and
$Ar_1$ and $Ar_2$ optionally have a substituent of a methyl group, an ethyl group, an iso-propyl group, a t-butyl group, or a fluorine atom.

2. The benzo[h]hexaphene according to claim 1, represented by the following Formula (2):

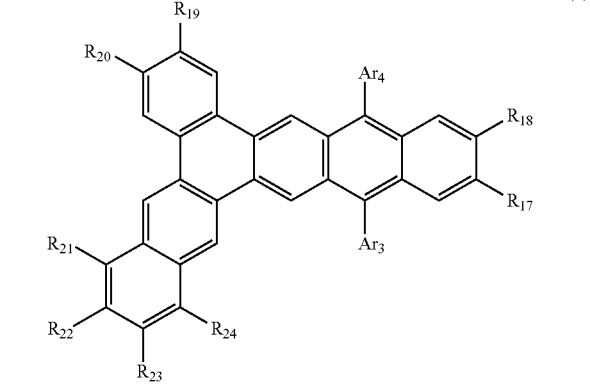

(2)

wherein,
$R_{17}$ to $R_{24}$ are each independently selected from a hydrogen atom, a halogen atom, a methyl group, an ethyl group, an iso-propyl group, a t-butyl group, a cyano group, a diphenylamino group, a pyridyl group, a phenyl group, a biphenyl group, a terphenyl group, and a naphthyl group;
the diphenylamino, pyridyl, phenyl, biphenyl, terphenyl, and naphthyl groups optionally have a substituent of a methyl group, an ethyl group, an iso-propyl group, a t-butyl group, or a fluorine atom;

Ar$_3$ and Ar$_4$ are any of a phenyl group, a biphenyl group, a terphenyl group, and a naphthyl group; and Ar$_3$ and Ar$_4$ optionally have a substituent of a methyl group, an ethyl group, an iso-propyl group, a t-butyl group, or a fluorine atom.

3. An organic light-emitting device comprising a cathode, an anode, and an organic compound layer disposed between the anode and the cathode, wherein the organic compound layer includes at least one layer including an organic compound according to claim 1.

4. The organic light-emitting device according to claim 3, wherein the organic compound layer is a light-emitting layer.

5. The organic light-emitting device according to claim 4, wherein the light-emitting layer includes a host material and a guest material, and the host material is the benzo[h]hexaphene.

6. An organic light-emitting device according to claim 3, wherein the organic compound layer includes a light-emitting portion including a plurality of organic compounds;

at least one of the plurality of organic compounds is the benzo[h]hexaphene; and the light-emitting portion emits white light.

7. A display apparatus comprising:

a plurality of pixels each including an organic light-emitting device according to claim 3 and an active device connected to the organic light-emitting device.

8. The display apparatus according to claim 7, wherein the organic light-emitting device is disposed on a substrate; and the active device is disposed in the substrate.

9. An image display apparatus comprising an input section for inputting image information and a display section for displaying an image, wherein the display section is a display apparatus according to claim 8.

10. A lighting system comprising:

an organic light-emitting device according to claim 3; and an AC/DC converter circuit connected to the organic light-emitting device.

11. An image-forming apparatus comprising:

a photosensitive member;

a charging unit for charging a surface of the photosensitive member;

an exposure unit for forming an electrostatic latent image by exposing the photosensitive member; and a developing unit for developing the electrostatic latent image formed on the surface of the photosensitive member, wherein the exposure unit includes an organic light-emitting device according to claim 3.

12. An exposure light source of an electrophotographic image forming apparatus comprising the organic light-emitting device according to claim 3.

* * * * *